US012606521B2

(12) United States Patent
Bellacosa et al.

(10) Patent No.: US 12,606,521 B2
(45) Date of Patent: Apr. 21, 2026

(54) METHODS OF TREATING CANCER

(71) Applicant: Institute For Cancer Research, Philadelphia, PA (US)

(72) Inventors: Alfonso Bellacosa, Philadephia, PA (US); John Karanicolas, Philadelphia, PA (US); Timothy J. Yen, Philadelphia, PA (US); Michael Cory, Philadelphia, PA (US); Chris Parry, Philadelphia, PA (US); Rahul Prasad, Philadelphia, PA (US)

(73) Assignee: Institute For Cancer Research, Philadelphia, PA (US)

( * ) Notice: Subject to any disclaimer, the term of this patent is extended or adjusted under 35 U.S.C. 154(b) by 491 days.

(21) Appl. No.: 18/043,548

(22) PCT Filed: Aug. 30, 2021

(86) PCT No.: PCT/US2021/048187

§ 371 (c)(1),
(2) Date: Feb. 28, 2023

(87) PCT Pub. No.: WO2022/047288

PCT Pub. Date: Mar. 3, 2022

(65) Prior Publication Data

US 2024/0190817 A1 Jun. 13, 2024

Related U.S. Application Data

(60) Provisional application No. 63/108,299, filed on Oct. 31, 2020, provisional application No. 63/072,262, filed on Aug. 31, 2020.

(51) Int. Cl.

| | |
|---|---|
| ***C07C 311/21*** | (2006.01) |
| ***A61K 31/18*** | (2006.01) |
| ***A61K 31/4439*** | (2006.01) |
| ***C07D 401/12*** | (2006.01) |

(52) U.S. Cl.
CPC ............ *C07C 311/21* (2013.01); *A61K 31/18* (2013.01); *A61K 31/4439* (2013.01); *C07D 401/12* (2013.01)

(58) Field of Classification Search
CPC ..................................................... C07C 311/21
See application file for complete search history.

(56) References Cited

U.S. PATENT DOCUMENTS

2011/0190302 A1 8/2011 Grieg et al.

FOREIGN PATENT DOCUMENTS

| | | |
|---|---|---|
| CA 3191223 | | 8/2021 |
| EP 21862906.1 | | 8/2021 |
| WO WO PCT/US2021/048187 | | 8/2021 |

OTHER PUBLICATIONS

Clare et al.(1999) : STN International, CAPLUS database, Accession No. 1999 : 615750.*
Pubchem SID 228429726; Feb. 12, 2015; https://pubchem.ncbi.nlm.nih.gov/substance/228429726.
He, et al. (2011) "Tet-Mediated Formation of 5-Carboxylcytosine and its Excision by TDB in Mammalian DNA," *Science*, 333 (6047): 1303-1307.
Ito, et al. (2018) "Regulation of Cellular Senescience by Polycomb Chromatin Modifiers Through Distinct DNA Damage-and Histone Methylation-Dependent Pathways" *Cell Rep.* 22(13): 3480-3492.
Johnson, et al. (2016) "Ultra-High-throughput Structure-Based Virtual Screening for Small-Molecule Inhibitors of Protein-Protein Interactions" *J. Chem Inf. Model*, 56(2):399-411.
Maiti, et al. (2011) "Thymine DNA Glycosylase can Rapidly Excise 5-Formylcytosine and 5-Carboxylcytosine: Potential Implications for Active Demethylation of CpG Sites;" *J. Biol. Chem.*, 286 (41): 35334-35338.
Mancuso, et al. (2019) "Thymine DNA Glycosylase as a Novel Target for Melanoma," *Oncogene*, 38(19): 3710-3728.
Narita, et al. (2003) "Rb-Mediated Heterochromatin Formation and Silencing of E2F Target Genes During Cellular Senescence" *Cell*, 113(6): 703-716.
Zhang et al. (2007) "Molecular Dissection of Formation of Senscience-Associated Heterochromatin Foci" *Mo. Cell. Biol.* 27(6): 2343-2358.
Zhang et al. (2012) "Thymine DNA Glycosylase Specifically Recognizes 5-Carboxylcytosine-modified DNA" *Nat. Chem Biol.*, 8(4): 328-330.
U.S. Appl. No. 63/072,262, filed Aug. 31, 2020, Alfonso Bellacosa.
U.S. Appl. No. 63/108,299, filed Oct. 31, 2020, Alfonso Bellacosa.

* cited by examiner

*Primary Examiner* — Golam M Shameem
(74) *Attorney, Agent, or Firm* — Ballard Spahr LLP

(57) ABSTRACT

Phenylsulfonamido compounds that inhibit genome-wide hypomethylation and can be used to treat cancer, including melanoma, prostate cancer, pancreatic cancer, breast cancer, colon cancer, lung cancer, ovarian cancer, and glioblastoma, are provided.

10 Claims, 22 Drawing Sheets

Specification includes a Sequence Listing.

A.

B.

C.

Mft68 flox/flox
est. IC50 = 172.17

Mft68 flox/-
est. IC50 = 88.33

A.

B.

A.

MC1 treatment of H23 lung cancer cells

B.

A.

B.

C.

A.

B.

SK28 (melanoma)

METHODS OF TREATING CANCER

CROSS-REFERENCE TO RELATED APPLICATIONS

This Application is a U.S. National Phase Application of International Application No. PCT/US2021/048187, filed on Aug. 30, 2021, which claims the benefit of U.S. Application No. 63/108,299, filed on Oct. 31, 2020, and U.S. Application No. 63/072,262, filed on Aug. 31, 2020, the contents of which are hereby incorporated by reference in their entireties.

REFERENCE TO GOVERNMENT GRANTS

This invention was made with government support under Grant Nos. CA078412 and CA191956 awarded by the National Institutes of Health, and Grant No. W81XWH-17-1-0136 awarded by the Department of Defense. The government has certain rights in the invention.

REFERENCE TO SEQUENCE LISTING

The Sequence Listing submitted Aug. 4, 2023 as a text file named 38235_0005U3_ST25.txt, created on Aug. 3, 2023, and having a size of 967 bytes is hereby incorporated by reference pursuant to 37 C.F.R. §§ 1.831-1.835.

FIELD

The present disclosure is directed, in part, to phenylsulfonamido compounds and method of treating cancer with the same. More particularly, the disclosure is directed to inhibiting the expression or biologic activity of thymine DNA glycosylase (TDG) in cancer cells characterized by genome-wide hypomethylation.

BACKGROUND

Two known epigenetic alterations in cancer are CpG island methylation (also referred to as CpG island methylator phenotype, or CIMP) and genome-wide hypomethylation. In particular, about 20-40% of melanomas, triple-negative breast cancers, serious ovarian and serious endometrial cancers are characterized by a pervasive genome-wide hypomethylation that can be documented by mining the TCGA methylation data. Approximately 15 to 20% of non-small cell lung cancer in TCGA (LUAD and LUSC datasets) are also characterized by prominent DNA hypomethylation. Demethylating agents (e.g., decitabine and azacytidine) are an effective epigenetic therapy of cancer that target the CIMP phenotype with the intention of reactivating the expression of genes silenced by hypermethylation. However, there has been no effort to specifically target the genome-wide hypomethylation in cancer. It has been established that cancers with prominent genome-wide hypomethylation exhibit elevated expression of DNA demethylases TDG and TET1, TET2 or TET3 working in pathways of active DNA demethylation. Accordingly, cancers with prominent genome-wide hypomethylation may benefit from inhibition of demethylases. Inhibition of these demethylases is expected to antagonize, correct and reprogram the genome-wide hypomethylation, thus suppressing oncogenic pathways and achieving a therapeutic benefit. This would include all cancers that exhibit prominent genome wide hypomethylation with activation of oncogenic pathways, for which the term onco-epigenetic alterations is applied.

TDG inhibitors may target different epigenomic areas than conventional DNA hypomethylating agents. Specifically, TDG knockdown induces hypermethylation in melanoma cell lines, and the TDG inhibitor closantel synergizes with decitabine in killing cancer cells, which implies that closantel has an effect on a different epigenetic space than decitabine. Accordingly, it is desirable to identify additional TDG inhibitors that are suitable for treatment of genome-wide hypomethylation-associated diseases, such as cancer.

SUMMARY

The present disclosure provides compounds having Formula I:

(I)

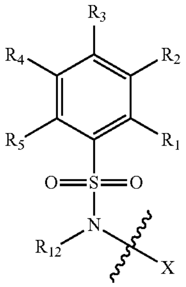

or a pharmaceutically acceptable salt thereof, wherein: X is

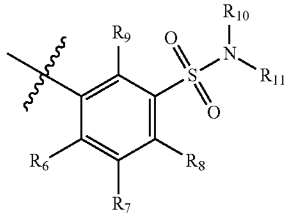

or

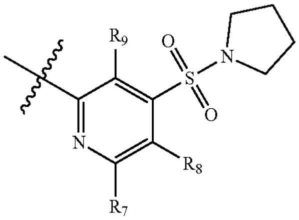

;

each of $R_1$, $R_2$, $R_3$, $R_4$, and $R_5$ is, independently, selected from the group consisting of hydrogen, halogen, hydroxyl, cyano, nitro, substituted or unsubstituted alkyl, substituted or unsubstituted alkenyl, substituted or unsubstituted alkoxy, substituted or unsubstituted amine, substituted or unsubstituted alkylamino, substituted or unsubstituted aminoalkoxy, and substituted or unsubstituted alkylthio; $R_6$ is selected from the group consisting of hydrogen, halogen, hydroxyl, cyano, nitro, substituted or unsubstituted alkyl, substituted or unsubstituted alkoxy, substituted or unsubstituted amine, substituted or unsubstituted alkylamino, and substituted or unsubstituted aminoalkoxy; each of $R_7$, $R_8$, $R_9$, and $R_{12}$ is, independently, selected from the group consisting of hydrogen, halogen, hydroxyl, cyano, nitro, substituted or unsubstituted alkyl, substituted or unsubstituted alkoxy, and substituted or unsubstituted amine; and $R_{10}$ and $R_{11}$ are, independently, selected from the group consisting of hydrogen, substituted or unsubstituted alkyl, and substituted or unsubstituted cycloalkyl, or together with the nitrogen to which they are bonded form a substituted or unsubstituted heteroaryl or a substituted or unsubstituted heterocycloalkyl.

The present disclosure also provides pharmaceutical compositions comprising any one or more of these compounds, or a pharmaceutically acceptable salt thereof, and a pharmaceutically acceptable carrier.

The present disclosure also provides methods of treating a mammal having cancer comprising administering to the mammal any one or more of these compounds, or a pharmaceutically acceptable salt thereof, or a composition comprising any one or more of these compounds, or a pharmaceutically acceptable salt thereof.

The present disclosure also provides uses of any one or more of these compounds, or a pharmaceutically acceptable salt thereof, or a composition comprising any one or more of these compounds, or a pharmaceutically acceptable salt thereof, for treating a mammal having cancer.

The present disclosure also provides uses of any one or more of these compounds, or a pharmaceutically acceptable salt thereof, or a composition comprising any one or more of these compounds, or a pharmaceutically acceptable salt thereof, in the preparation of a medicament for treating a mammal having cancer.

DESCRIPTION OF EMBODIMENTS

Figure 1:
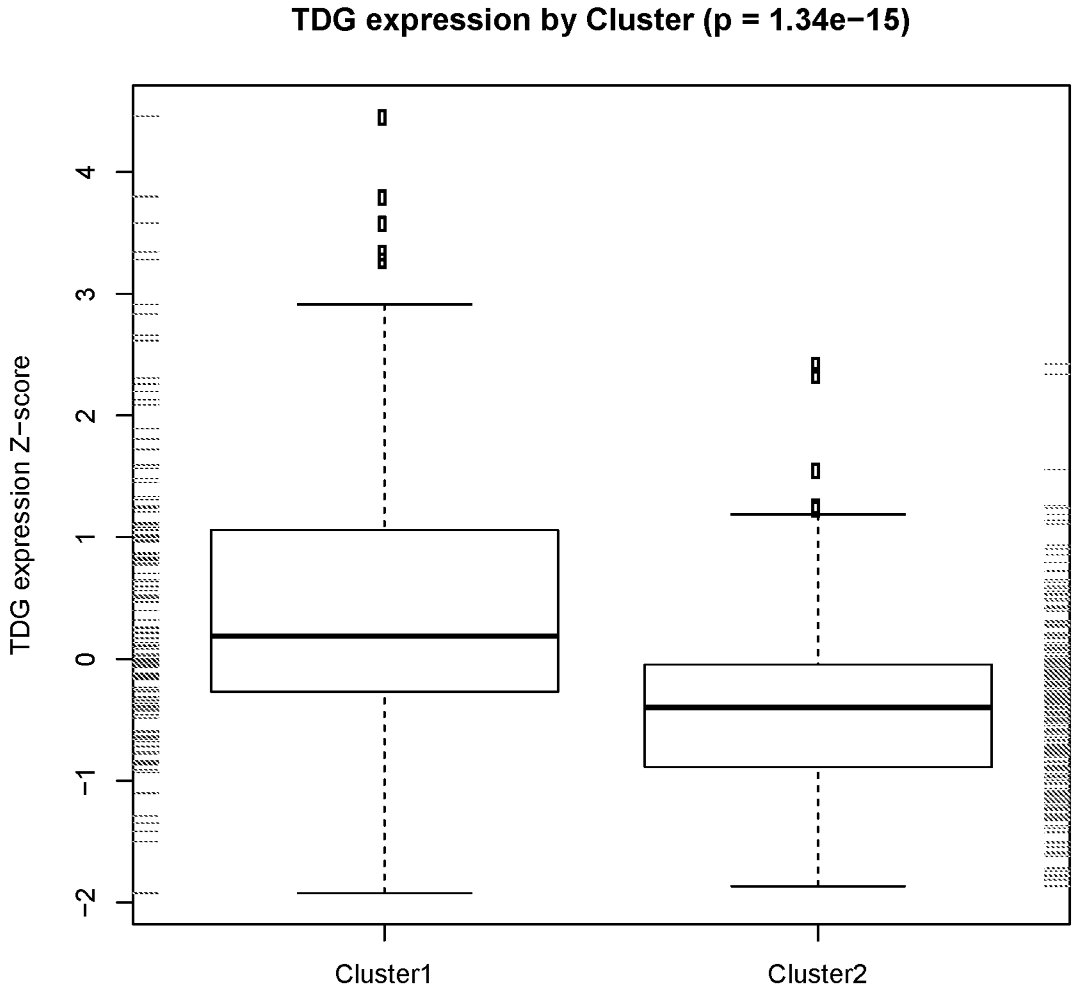
FIG. 1 depicts the SKCM TCGA metastatic melanoma cluster with lower methylation has higher expression of TDG, TETs, DNMT3A/B & APE; boxplots depicting comparisons of TDG, APE and TET1-3 gene expression in the two SKCM TCGA metastatic melanoma clusters (Wilcoxon rank sum test p-values, all significant, are shown).
Figure 1:
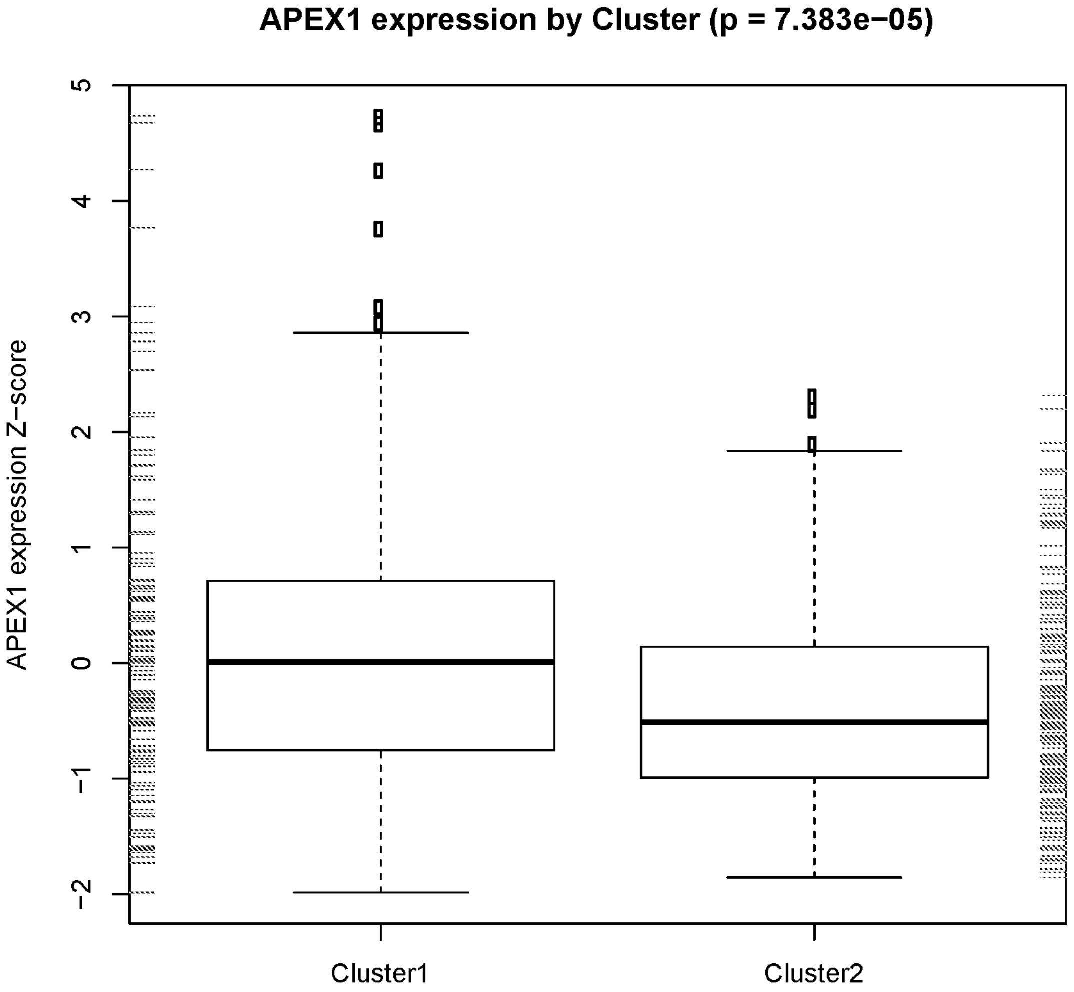
Figure 1:
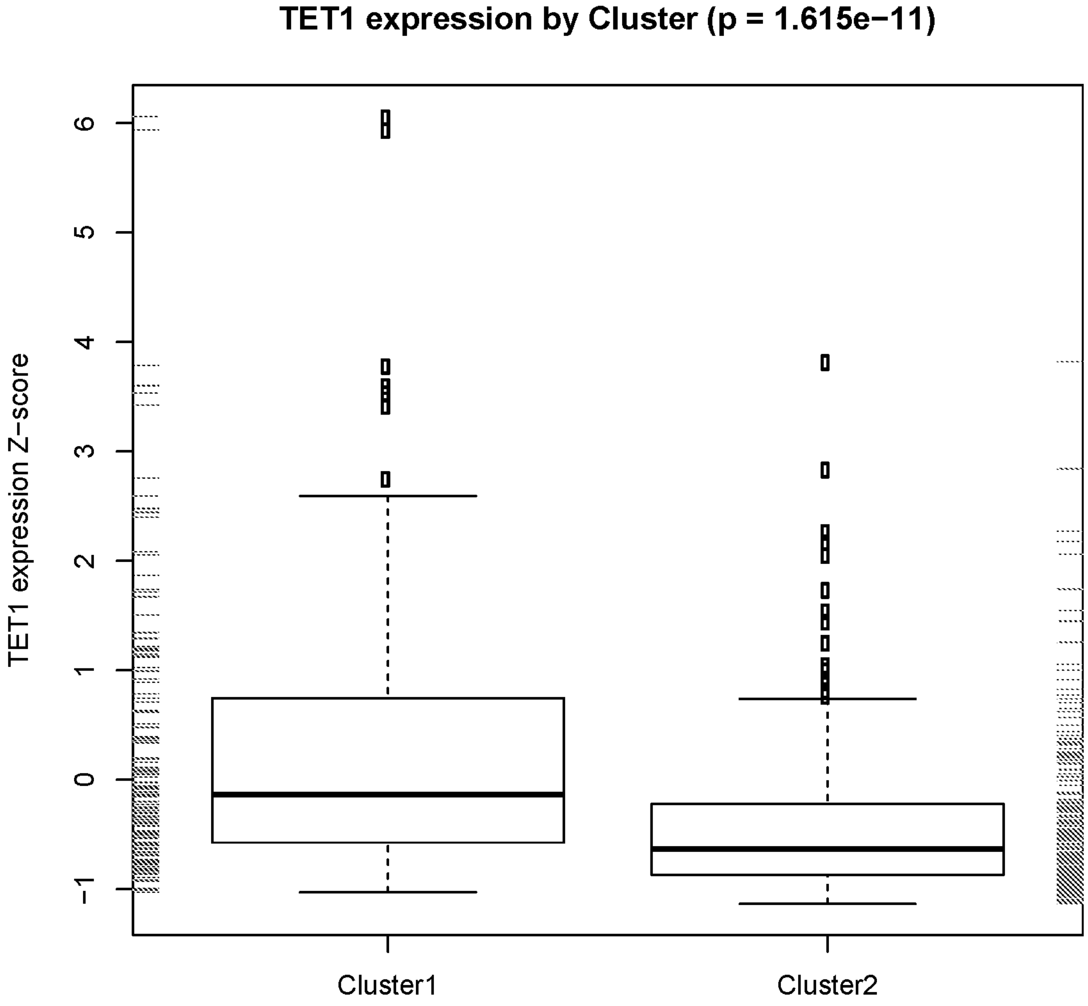
Figure 1:
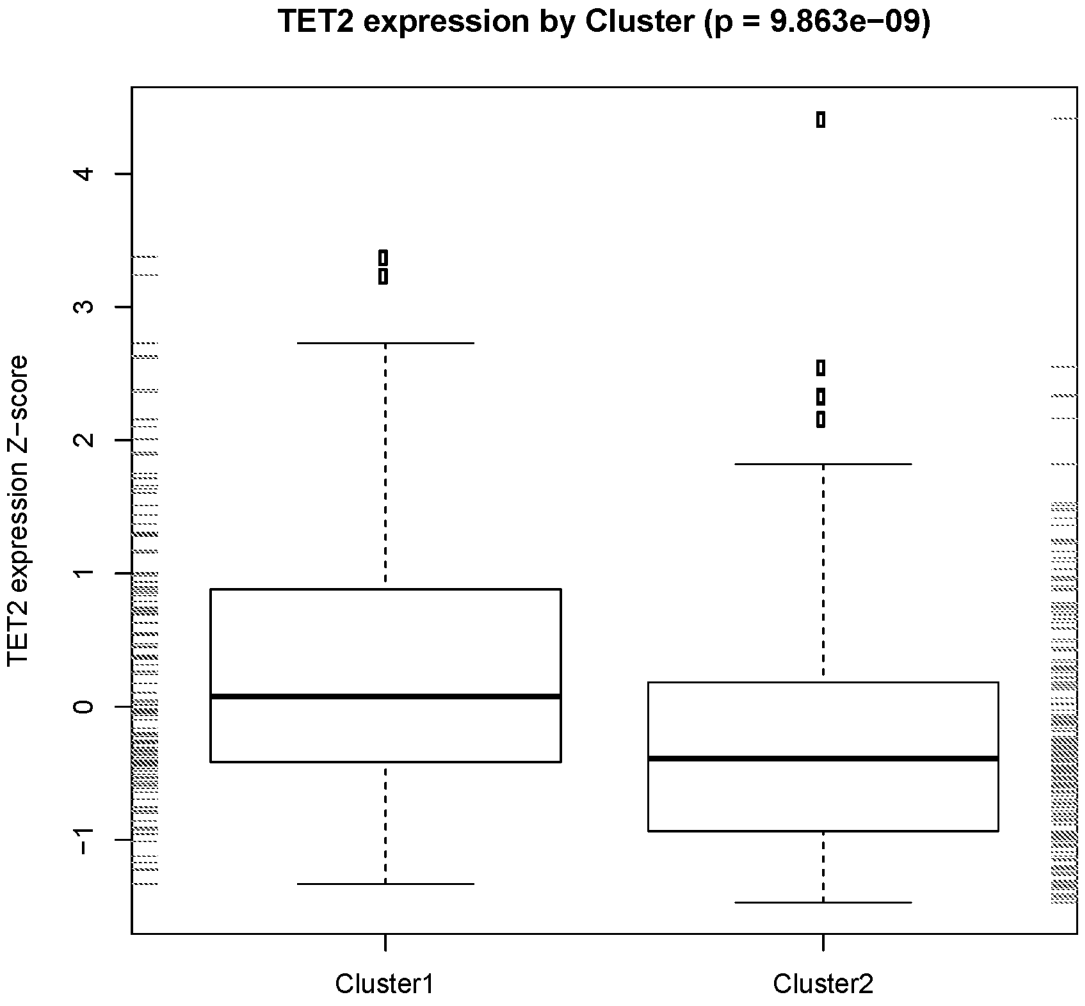
Figure 1:
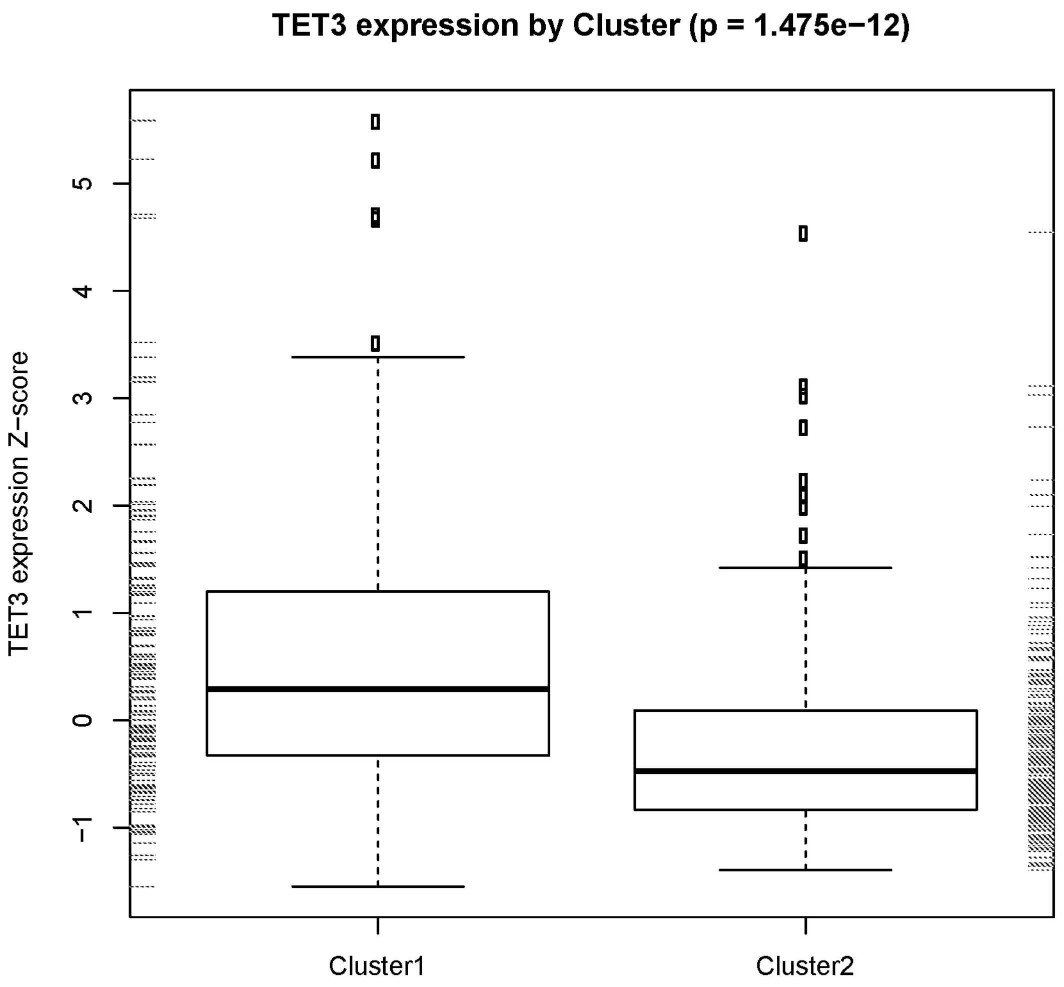

Unless defined otherwise, all technical and scientific terms have the same meaning as is commonly understood by one of ordinary skill in the art to which the disclosed embodiments belong.

As used herein, the terms "a" or "an" mean "at least one" or "one or more" unless the context clearly indicates otherwise.

As used herein, the term "about" means that the recited numerical value is approximate and small variations would not significantly affect the practice of the disclosed embodiments. Where a numerical value is used, unless indicated otherwise by the context, "about" means the numerical value can vary by +10% and remain within the scope of the disclosed embodiments.

As used herein, the term "alkenyl" means a straight or branched alkyl group having 2 to 20 carbon atoms and having one or more double carbon-carbon bonds. In some embodiments, the alkenyl group has from 2 to 10 carbon atoms, from 2 to 8 carbon atoms, from 2 to 6 carbon atoms, from 2 to 4 carbon atoms, from 3 to 10 carbon atoms, from 3 to 8 carbon atoms, from 3 to 6 carbon atoms, or 3 or 4 carbon atoms. Examples of alkenyl groups include, but are not limited to, ethenyl, 1-propenyl, 2-methyl-1-propenyl, 2-propenyl, 1-butenyl, 2-butenyl, and the like.

As used herein, the term "alkoxy" means a straight or branched —O-alkyl group having 1 to 20 carbon atoms. In some embodiments, the alkoxy group has from 1 to 10 carbon atoms, from 1 to 8 carbon atoms, from 1 to 6 carbon atoms, from 1 to 4 carbon atoms, from 2 to 10 carbon atoms, from 2 to 8 carbon atoms, from 2 to 6 carbon atoms, or from 2 to 4 carbon atoms. Examples of alkoxy groups include, but are not limited to, methoxy, ethoxy, n-propoxy, isopropoxy, t-butoxy, and the like.

As used herein, the term "alkyl" means a saturated hydrocarbon group which is straight-chained or branched. In some embodiments, the alkyl group has from 1 to 20 carbon atoms, from 2 to 20 carbon atoms, from 1 to 10 carbon atoms, from 2 to 10 carbon atoms, from 1 to 8 carbon atoms, from 2 to 8 carbon atoms, from 1 to 6 carbon atoms, from 2 to 6 carbon atoms, from 1 to 4 carbon atoms, from 2 to 4 carbon atoms, from 1 to 3 carbon atoms, or 2 or 3 carbon atoms. Examples of alkyl groups include, but are not limited to, methyl (Me), ethyl (Et), propyl (e.g., n-propyl and isopropyl), butyl (e.g., n-butyl, t-butyl, isobutyl), pentyl (e.g., n-pentyl, isopentyl, neopentyl), hexyl, isohexyl, heptyl, octyl, nonyl, 4,4-dimethylpentyl, 2,2,4-trimethylpentyl, decyl, undecyl, dodecyl, 2-methyl-1-propyl, 2-methyl-2-propyl, 2-methyl-1-butyl, 3-methyl-1-butyl, 2-methyl-3-butyl, 2-methyl-1-pentyl, 2,2-dimethyl-1-propyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, and the like.

As used herein, the term "alkylamino" means an amino group substituted by an alkyl group. In some embodiments, the alkyl group is a lower alkyl group having from 1 to 6 carbon atoms. Alkylamino groups include, but are not limited to, $—NHCH_2CH_3$, $—NH(CH_2)_2CH_3$, $—NH(CH_2)_3CH_3$, $—NH(CH_2)_4CH_3$, and $—NH(CH_2)_5CH_3$, and the like.

As used herein, the term "alkylthio" means an —S-alkyl group having from 1 to 6 carbon atoms. Alkylthio groups include, but are not limited to, $—SCH_2CH_3$, $—S(CH_2)_2CH_3$, $—S(CH_2)_3CH_3$, $—S(CH_2)_4CH_3$, and $—S(CH_2)_5CH_3$, and the like.

As used herein, the term "amino" means $—NH_2$.

As used herein, the term "aminoalkoxy" means an alkoxy group substituted by an amino group. Examples of aminoalkoxy groups include, but are not limited to, $—OCH_2NH_2$, $—OCH_2CH_2NH_2$, $—O(CH_2)_3NH_2$, and $—O(CH_2)_4NH_2$, and the like.

As used herein, the term "carrier" means a diluent, adjuvant, or excipient with which a compound is administered in a composition.

As used herein, the term, "compound" means all stereoisomers, tautomers, isotopes, and polymorphs of the compounds described herein.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive and open-ended and include the options following the terms, and do not exclude additional, unrecited elements or method steps.

As used herein, the term "cyano" means —CN.

As used herein, the term "cycloalkyl" means non-aromatic cyclic hydrocarbons including cyclized alkyl, alkenyl, and alkynyl groups that have up to 20 ring-forming carbon atoms. Cycloalkyl groups have from 3 to 15 ring-forming carbon atoms, from 3 to 10 ring-forming carbon atoms, from 3 to 8 ring-forming carbon atoms, from 3 to 6 ring-forming carbon atoms, from 4 to 6 ring-forming carbon atoms, from 3 to 5 ring-forming carbon atoms, or 5 or 6 ring-forming carbon atoms. Ring-forming carbon atoms of a cycloalkyl group can be optionally substituted by oxo or sulfido. Cycloalkyl groups include, but are not limited to, monocyclic or polycyclic ring systems such as fused ring systems, bridged ring systems, and spiro ring systems. In some embodiments, polycyclic ring systems include 2, 3, or 4 fused rings. Examples of cycloalkyl groups include, but are not limited to, cyclopropyl, cyclobutyl, cyclopentyl, cyclohexyl, cycloheptyl, cyclooctyl, cyclononyl, cyclopentenyl, cyclohexenyl, cyclohexadienyl, cycloheptatrienyl, norbornyl, norpinyl, norcarnyl, adamantyl, and the like. Cycloalkyl groups can also have one or more aromatic rings fused (having a bond in common with) to the cycloalkyl ring such as, for example, benzo or thienyl derivatives of pentane, pentene, hexane, and the like (e.g., 2,3-dihydro-1H-indene-1-yl, or 1H-inden-2(3H)-one-1-yl).

As used herein, the term "halogen" includes, but is not limited to, fluoro, chloro, bromo, and iodo.

As used herein, the term "heteroaryl" means an aromatic heterocycle having up to 20 ring-forming atoms (e.g., C) and having at least one heteroatom ring member (ring-forming atom) such as sulfur, oxygen, or nitrogen. In some embodiments, the heteroaryl group has at least one or more heteroatom ring-forming atoms, each of which are, independently, sulfur, oxygen, or nitrogen. In some embodiments, the heteroaryl group has from 3 to 20 ring-forming atoms, from 3 to 10 ring-forming atoms, from 3 to 6 ring-forming atoms, or from 3 to 5 ring-forming atoms. In some embodiments, the heteroaryl group contains 2 to 14 carbon atoms, from 2 to 7 carbon atoms, or 5 or 6 carbon atoms. In some embodiments, the heteroaryl group has 1 to 4 heteroatoms, 1 to 3 heteroatoms, or 1 or 2 heteroatoms. Heteroaryl groups include monocyclic and polycyclic (e.g., having 2, 3 or 4 fused rings) systems. Examples of heteroaryl groups include, but are not limited to, pyridyl, pyrimidinyl, pyrazinyl, pyridavinyl, pyridinyl (including 2-aminopyridine), triazinyl, furyl, quinolyl, isoquinolyl, thienyl, imidazolyl, thiazolyl, indolyl (such as indol-3-yl), pyrryl, oxazolyl, benzofuryl, benzothienyl, pyrazolyl, benzthiazolyl, isoxazolyl, triazolyl (including 1,2,4-triazole, 1,2,3-triazole, and 5-amino-1,2,4-triazole), tetrazolyl, indazolyl, isothiazolyl, 1,2,4-thiadiazolyl, benzothienyl, purinyl, carbazolyl, isoxazolyl, benzimidazolyl, indolinyl, pyranyl, pyrazolyl, triazolyl, oxadiazolyl (including 1,2,3-oxadiazole, 1,2,4-oxadiazole, 1,2,5-oxadiazole, 3-amino-1,2,4-oxadiazole, 1,3,4-oxadiazole), thianthrenyl, indolizinyl, isoindolyl, isobenzofuranyl, pyrrolyl, benzoxazolyl, xanthenyl, 2H-pyrrolyl, 3H-indolyl, 4H-quinolizinyl, phthalazinyl, acridinyl, naphthyridinyl, quinazolinyl, phenanthridinyl, perimidinyl, phenanthrolinyl, phenavinyl, isothiazolyl, phenothiazinyl, isoxazolyl, furazanyl, phenoxazinyl groups, and the like.

As used herein, the term "heterocycloalkyl" means non-aromatic cyclic hydrocarbons including cyclized alkyl, alkenyl, and alkynyl groups that have up to 20 ring-forming carbon atoms, and having at least one heteroatom ring member (ring-forming atom) such as sulfur, oxygen, or nitrogen. Hetereocycloalkyl groups have from 3 to 15 ring-forming carbon atoms, from 3 to 10 ring-forming carbon atoms, from 3 to 8 ring-forming carbon atoms, from 3 to 6 ring-forming carbon atoms, from 4 to 6 ring-forming carbon atoms, from 3 to 5 ring-forming carbon atoms, or 5 or 6 ring-forming carbon atoms. Ring-forming carbon atoms of a heterocycloalkyl group can be optionally substituted by oxo or sulfido. Heterocycloalkyl groups include, but are not limited to, monocyclic or polycyclic ring systems such as fused ring systems, bridged ring systems, and spiro ring systems. In some embodiments, polycyclic ring systems include 2, 3, or 4 fused rings. Examples of heterocycloalkyl groups include, but are not limited to, piperidine, pyrrolidine, piperazine, morpholine, lactones, lactams, and the like.

As used herein, the term "hydroxy" or "hydroxyl" means an —OH group.

As used herein, the phrase "in need thereof" means that the "individual," "subject," or "patient" has been identified as having a need for the particular method, prevention, or treatment. In some embodiments, the identification can be by any means of diagnosis. In any of the methods, preventions, and treatments described herein, the "individual," "subject," or "patient" can be in need thereof.

As used herein, the term "mammal" means a rodent (i.e., a mouse, a rat, or a guinea pig), a monkey, a sheep, a cat, a dog, a cow, a horse, a pig, or a human. In some embodiments, the mammal is a human.

As used herein, the term "nitro" means $—NO_2$.

As used herein, the phrase "substituted" means that any hydrogen atom on the designated compound or ring can be replaced with a substituent group, provided that the normal valency of the designated compound or ring is not exceeded, and that the substitution results in a stable compound. For example, if a methyl group is optionally substituted, then 1, 2, or 3 hydrogen atoms on the carbon atom within the methyl group can be replaced with 1, 2, or 3 of the recited substituent groups.

As used herein, the phrase "pharmaceutically acceptable" means that the compounds, materials, compositions, and/or dosage forms are within the scope of sound medical judgment and are suitable for use in contact with tissues of humans and other animals. In some embodiments, "pharmaceutically acceptable" means approved by a regulatory agency of the Federal government or a state government or listed in the U.S. Pharmacopeia or other generally recognized pharmacopeia for use in animals, and more particularly in humans. In some embodiments, the pharmaceutically acceptable compounds, materials, compositions, and/or dosage forms result in no persistent detrimental effect on the subject, or on the general health of the subject being treated. However, it will be recognized that transient effects, such as minor irritation or a "stinging" sensation, are common with administration of medicament and the existence of such transient effects is not inconsistent with the composition, formulation, or ingredient (e.g., excipient) in question.

As used herein, the phrase "pharmaceutically acceptable salt(s)," includes, but is not limited to, salts of acidic or basic groups. Compounds that are basic in nature are capable of forming a wide variety of salts with various inorganic and organic acids. Acids that may be used to prepare pharmaceutically acceptable acid addition salts of such basic compounds are those that form non-toxic acid addition salts, i.e., salts containing pharmacologically acceptable anions including, but not limited to, sulfuric, thiosulfuric, citric, maleic, acetic, oxalic, hydrochloride, hydrobromide, hydroiodide, nitrate, sulfate, bisulfate, bisulfite, phosphate, acid phosphate, isonicotinate, borate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, bicarbonate, malonate, mesylate, esylate, napsydisylate, tosy late, besylate, orthophoshate, trifluoroacetate, and pamoate (i.e., 1,1'-methylene-bis-(2-hydroxy-3-naphthoate)) salts. Compounds that include an amino moiety may form pharmaceutically acceptable salts with various amino acids, in addition to the acids mentioned above. Compounds that are acidic in nature are capable of forming base salts with various pharmacologically acceptable cations. Examples of such salts include, but are not limited to, alkali metal or alkaline earth metal salts and, particularly, calcium, magnesium, ammonium, sodium, lithium, zinc, potassium, and iron salts. Salts also includes quaternary ammonium salts of the compounds described herein, where the compounds have one or more tertiary amine moiety.

As used herein, the terms "treat." "treated," or "treating" mean both therapeutic treatment and prophylactic or preventative measures wherein the object is to prevent or slow down (lessen) an undesired physiological condition, disorder or disease, or obtain beneficial or desired clinical results. For purposes herein, beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease. Treatment includes eliciting a clinically significant response, optionally without excessive levels of side effects. Treatment also includes prolonging survival as compared to expected survival if not receiving treatment.

At various places herein, substituents of compounds may be disclosed in groups or in ranges. It is specifically intended that the disclosure include each and every individual subcombination of the members of such groups and ranges. For example, the term "$C_1$-$_6$alkyl" is specifically intended to individually disclose methyl, ethyl, propyl, $C_4$alkyl, $C_5$alkyl, and $C_6$alkyl.

It should be appreciated that particular features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable subcombination.

The compounds described herein also include hydrates and solvates, as well as anhydrous and non-solvated forms.

The compounds described herein can also include all isotopes of atoms occurring in the intermediates or final compounds. Isotopes include those atoms having the same atomic number but different mass numbers. For example, isotopes of hydrogen include tritium and deuterium. Carbon ($^{12}C$) can be replaced at any position with $^{13}C$ or $^{14}C$. Nitrogen ($^{14}N$) can be replaced with $^{15}N$. Oxygen ($^{16}O$) can be replaced at any position with $^{17}O$ or $^{18}O$. Sulfur ($^{32}S$) can be replaced with $^{33}S$, $^{34}S$ or $^{36}S$. Chlorine ($^{35}Cl$) can be replaced with $^{37}Cl$. Bromine ($^{79}Br$) can be replaced with $^{81}Br$.

In some embodiments, the compounds, or salts thereof, are substantially isolated. Partial separation can include, for example, a composition enriched in any one or more of the compounds described herein. Substantial separation can include compositions containing at least about 50%, at least about 60%, at least about 70%, at least about 80%, at least about 90%, at least about 95%, at least about 97%, or at least about 99% by weight of any one or more of the compounds described herein, or salt thereof. Methods for isolating compounds and their salts are routine in the art.

Although the disclosed compounds are suitable in their present form, functional groups can be incorporated into the compounds with an expectation of similar results. In particular, thioamides and thioesters are anticipated to have very similar properties. The distance between aromatic rings can impact the geometrical pattern of the compound and this distance can be altered by incorporating aliphatic chains of varying length, which can be optionally substituted or can comprise an amino acid, a dicarboxylic acid or a diamine. The distance between and the relative orientation of monomers within the compounds can also be altered by replacing the amide bond with a surrogate having additional atoms. Thus, replacing a carbonyl group with a dicarbonyl alters the distance between the monomers and the propensity of dicarbonyl unit to adopt an anti arrangement of the two carbonyl moiety and alter the periodicity of the compound. Pyromellitic anhydride represents still another alternative to simple amide linkages which can alter the conformation and physical properties of the compound. Modern methods of solid phase organic chemistry (E. Atherton and R. C. Sheppard, Solid Phase Peptide Synthesis A Practical Approach IRL Press Oxford 1989) now allow the synthesis of homodisperse compounds with molecular weights approaching 5,000 Daltons. Other substitution patterns are equally effective.

The compounds described herein also include derivatives referred to as prodrugs, which can be prepared by modifying functional groups present in the compounds in such a way that the modifications are cleaved, either in routine manipulation or in vivo, to the parent compounds. Examples of prodrugs include compounds as described herein that contain one or more molecular moieties appended to a hydroxyl, amino, sulfhydryl, or carboxyl group of the compound, and that when administered to a patient, cleaves in vivo to form the free hydroxyl, amino, sulfhydryl, or carboxyl group, respectively. Examples of prodrugs include, but are not limited to, acetate, formate and benzoate derivatives of alcohol and amine functional groups in the compounds described herein. Preparation and use of prodrugs is discussed in T. Higuchi et al., "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are incorporated herein by reference in their entireties.

Compounds containing an amine function can also form N-oxides. A reference herein to a compound that contains an amine function also includes the N-oxide. Where a compound contains several amine functions, one or more than one nitrogen atom can be oxidized to form an N-oxide. Examples of N-oxides include N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g., a peroxy carboxylic acid) (see, Advanced Organic Chemistry, by Jerry March, 4th Edition, Wiley Interscience).

The present disclosure provides compounds having Formula I:

(I)

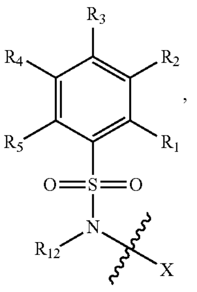

or a pharmaceutically acceptable salt thereof, wherein:

X is

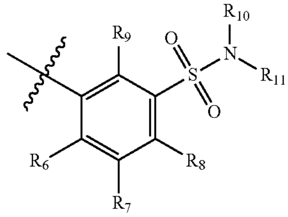

or

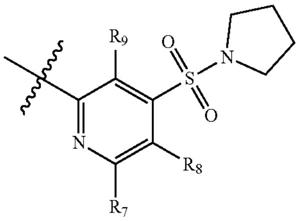

;

each of $R_1$, $R_2$, $R_3$, $R_4$, and $R_5$ is, independently, selected from the group consisting of hydrogen, halogen, hydroxyl, cyano, nitro, substituted or unsubstituted alkyl, substituted or unsubstituted alkenyl, substituted or unsubstituted alkoxy, substituted or unsubstituted amine, substituted or unsubstituted alkylamino, substituted or unsubstituted aminoalkoxy, and substituted or unsubstituted alkylthio;

$R_6$ is selected from the group consisting of hydrogen, halogen, hydroxyl, cyano, nitro, substituted or unsubstituted alkyl, substituted or unsubstituted alkoxy, substituted or unsubstituted amine, substituted or unsubstituted alkylamino, and substituted or unsubstituted aminoalkoxy;

each of $R_7$, $R_8$, $R_9$, and $R_{12}$ is, independently, selected from the group consisting of hydrogen, halogen, hydroxyl, cyano, nitro, substituted or unsubstituted alkyl, substituted or unsubstituted alkoxy, and substituted or unsubstituted amine; and $R_{10}$ and $R_{11}$ are, independently, selected from the group consisting of hydrogen, substituted or unsubstituted alkyl, and substituted or unsubstituted cycloalkyl, or together with the nitrogen to which they are bonded form a substituted or unsubstituted heteroaryl or a substituted or unsubstituted heterocycloalkyl.

In some embodiments, X is

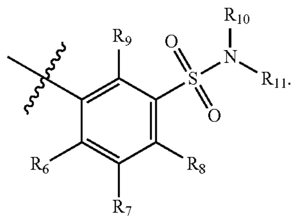

In some embodiments, each of $R_1$, $R_2$, $R_3$, $R_4$, and $R_5$ is, independently, selected from the group consisting of hydrogen, halogen, hydroxyl, cyano, nitro, substituted or unsubstituted alkyl, substituted or unsubstituted alkoxy, substituted or unsubstituted amine. In some embodiments, each of $R_1$, $R_2$, $R_3$, $R_4$, and $R_5$ is, independently, selected from the group consisting of hydrogen, halogen, hydroxyl, nitro, substituted or unsubstituted $C_{1-3}$alkyl, and substituted or unsubstituted $C_{1-3}$alkoxy. In some embodiments, each of $R_1$, $R_2$, $R_3$, $R_4$, and $R_5$ is, independently, selected from the group consisting of hydrogen, halogen, and substituted or unsubstituted $C_{1-3}$alkoxy. In some embodiments, each of $R_1$, $R_2$, $R_3$, $R_4$, and $R_5$ is, independently, hydrogen or unsubstituted $C_{1-3}$alkoxy. In some embodiments, each of $R_1$, $R_2$, $R_3$, $R_4$, and $R_5$ is, independently, hydrogen or —$OCH_3$. In some embodiments, $R_2$ and $R_4$ are —$OCH_3$, and $R_1$, $R_3$, and $R_5$ are hydrogen. In some embodiments, $R_2$ and $R_3$ are —$OCH_3$, and $R_1$, $R^4$, and $R_5$ are hydrogen. In some embodiments, $R_1$ and $R_2$ are —$OCH_3$, and $R_3$, $R_4$, and $R_5$ are hydrogen. In some embodiments, $R_1$ and $R_4$ are —$OCH_3$, and $R_2$, $R_3$, and $R_5$ are hydrogen.

In any of these embodiments, $R_6$ is selected from the group consisting of hydrogen, halogen, hydroxyl, nitro, substituted or unsubstituted alkyl, and substituted or unsubstituted alkoxy. In some embodiments, $R_6$ is selected from the group consisting of hydrogen, halogen, substituted or unsubstituted $C_{1-4}$alkyl, and substituted or unsubstituted $C_{1-4}$alkoxy. In some embodiments, $R_6$ is selected from the group consisting of hydrogen, unsubstituted $C_{1-3}$alkyl, and unsubstituted $C_{1-3}$alkoxy. In some embodiments, $R_6$ is selected from the group consisting of hydrogen, methyl, methoxy, ethoxy, —$OCH(CH_3)_2$.

In any of these embodiments, each of $R_7$, $R_8$, $R_9$, and $R_{12}$ is, independently, selected from the group consisting of hydrogen, halogen, hydroxyl, cyano, and nitro. In some embodiments, each of $R_7$, $R_8$, $R_9$, and $R_{12}$ is, independently, selected from the group consisting of hydrogen, halogen, and hydroxyl. In some embodiments, each of $R_7$, $R_8$, $R_9$, and $R_{12}$ is, independently, hydrogen or halogen.

In any of these embodiments, $R_{10}$ and $R_{11}$ are, independently, selected from the group consisting of hydrogen, substituted or unsubstituted alkyl, and substituted or unsubstituted cycloalkyl, or together with the nitrogen to which they are bonded form a substituted or unsubstituted heterocycloalkyl. In some embodiments, $R_{10}$ and $R_{11}$ are, independently, selected from the group consisting of hydrogen, unsubstituted $C_{1-4}$alkyl, and unsubstituted cycloalkyl, or together with the nitrogen to which they are bonded form an unsubstituted heterocycloalkyl. In some embodiments, $R_{10}$ and $R_{11}$ are, independently, selected from the group consisting of hydrogen, ethyl, or —$C(CH_3)_3$, or together with the nitrogen to which they are bonded form piperidine or pyrrolidine.

In some embodiments, each of $R_1$, $R_2$, $R_3$, $R_4$, and $R_5$ is, independently, selected from the group consisting of hydrogen, halogen, hydroxyl, cyano, nitro, substituted or unsubstituted alkyl, substituted or unsubstituted alkoxy, substituted or unsubstituted amine; $R_6$ is selected from the group consisting of hydrogen, halogen, hydroxyl, nitro, substituted or unsubstituted alkyl, and substituted or unsubstituted alkoxy; each of $R_7$, $R_8$, $R_9$, and $R_{12}$ is, independently, selected from the group consisting of hydrogen, halogen, hydroxyl, cyano, and nitro; and $R_{10}$ and $R_{11}$ are, independently, selected from the group consisting of hydrogen, substituted or unsubstituted alkyl, and substituted or unsubstituted cycloalkyl, or together with the nitrogen to which they are bonded form a substituted or unsubstituted heterocycloalkyl.

In some embodiments, each of $R_1$, $R_2$, $R_3$, $R_4$, and $R_5$ is, independently, selected from the group consisting of hydrogen, halogen, hydroxyl, nitro, substituted or unsubstituted $C_{1-3}$alkyl, and substituted or unsubstituted $C_{1-3}$alkoxy; $R_6$ is selected from the group consisting of hydrogen, halogen, substituted or unsubstituted $C_{1-4}$alkyl, and substituted or unsubstituted $C_{1-4}$alkoxy; each of $R_7$, $R_8$, $R_9$, and $R_{12}$ is, independently, selected from the group consisting of hydrogen, halogen, and hydroxyl; and $R_{10}$ and $R_{11}$ are, independently, selected from the group consisting of hydrogen, unsubstituted $C_{1-4}$alkyl, and unsubstituted cycloalkyl, or together with the nitrogen to which they are bonded form an unsubstituted heterocycloalkyl.

In some embodiments, each of $R_1$, $R_2$, $R_3$, $R_4$, and $R_5$ is, independently, selected from the group consisting of hydrogen, halogen, and substituted or unsubstituted $C_{1-3}$alkoxy; $R_6$ is selected from the group consisting of hydrogen, unsubstituted $C_{1-3}$alkyl, and unsubstituted $C_{1-3}$alkoxy; each of $R_7$, $R_8$, $R_9$, and $R_{12}$ is, independently, hydrogen or halogen; and $R_{10}$ and $R_{11}$ are, independently, selected from the group consisting of hydrogen, ethyl, or —$C(CH_3)_3$, or together with the nitrogen to which they are bonded form piperidine or pyrrolidine.

In some embodiments, each of $R_1$, $R_2$, $R_3$, $R_4$, and $R_5$ is, independently, hydrogen or unsubstituted $C_{1-3}$alkoxy; $R_6$ is selected from the group consisting of hydrogen, methyl, methoxy, ethoxy, —$OCH(CH_3)_2$; each of $R_7$, $R_8$, $R_9$, and $R_{12}$ is, independently, hydrogen or halogen; and $R_{10}$ and $R_{11}$ are, independently, selected from the group consisting of hydrogen, ethyl, or —$C(CH_3)_3$, or together with the nitrogen to which they are bonded form piperidine or pyrrolidine.

In some embodiments, each of $R_1$, $R_2$, $R_3$, $R_4$, and $R_5$ is, independently, hydrogen or —$OCH_3$; $R_6$ is selected from the group consisting of hydrogen, methyl, methoxy, ethoxy, —$OCH(CH_3)_2$; each of $R_7$, $R_8$, $R_9$, and $R_{12}$ is, independently, hydrogen or halogen; and $R_{10}$ and $R_{11}$ are, independently, selected from the group consisting of hydrogen, ethyl, or —$C(CH_3)_3$, or together with the nitrogen to which they are bonded form piperidine or pyrrolidine. In some embodiments, $R_2$ and $R_4$ are —$OCH_3$, and $R_1$, $R_3$, and $R_5$ are hydrogen. In some embodiments, $R_2$ and $R_3$ are —$OCH_3$, and $R_1$, $R_4$, and $R_5$ are hydrogen. In some embodiments, $R_1$ and $R_2$ are —$OCH_3$, and $R_3$, $R_4$, and $R_5$ are hydrogen. In some embodiments, $R_1$ and $R_4$ are —$OCH_3$, and $R_2$, $R_3$, and $R_5$ are hydrogen.

In some embodiments, the compound is selected from the group consisting of
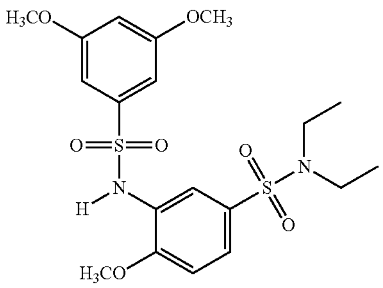
,
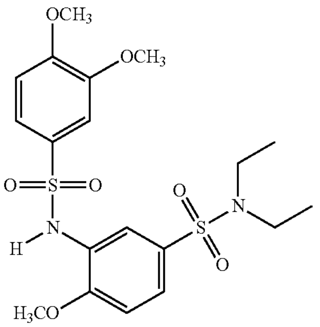
,
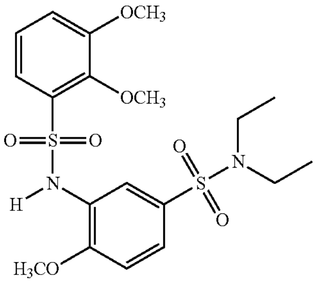
,
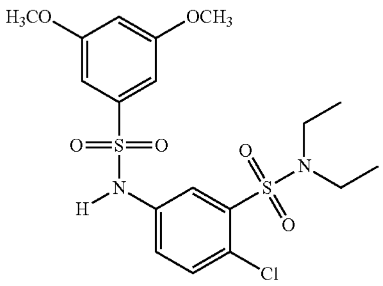
,
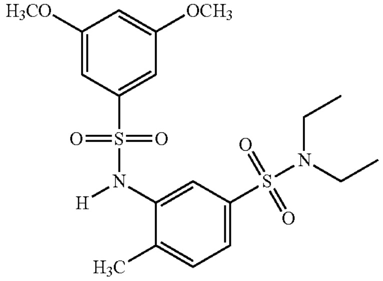
,
-continued
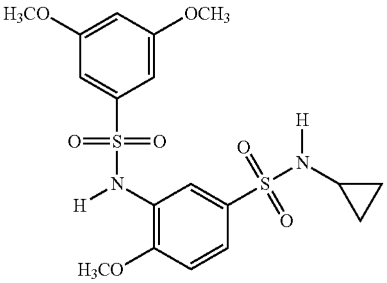
,
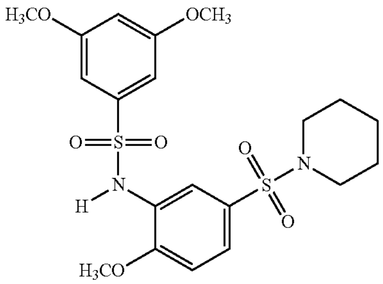
,
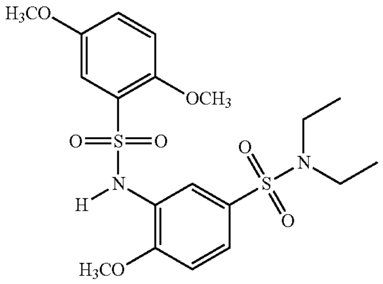
,
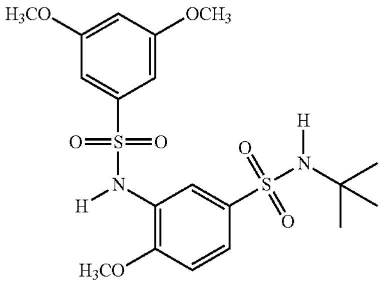
,
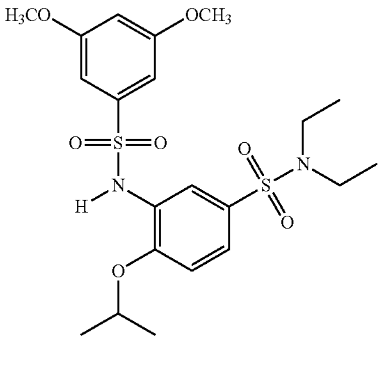
, and -continued

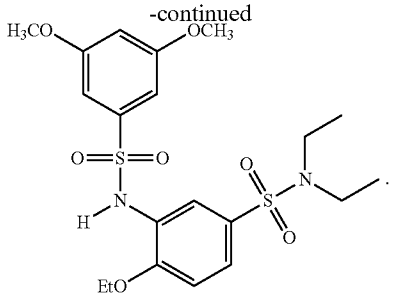

In some embodiments, X is

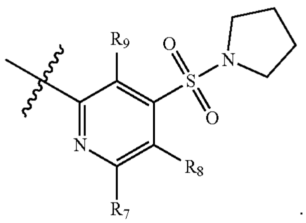

In some embodiments, each of $R_1$, $R_2$, $R_3$, $R_4$, and $R_5$ is, independently, selected from the group consisting of hydrogen, halogen, hydroxyl, cyano, nitro, substituted or unsubstituted alkyl, substituted or unsubstituted alkoxy, substituted or unsubstituted amine. In some embodiments, each of $R_1$, $R_2$, $R_3$, $R^4$, and $R_5$ is, independently, selected from the group consisting of hydrogen, halogen, hydroxyl, nitro, substituted or unsubstituted $C_{1-3}$alkyl, and substituted or unsubstituted $C_{1-3}$alkoxy. In some embodiments, each of $R_1$, $R_2$, $R_3$, $R^4$, and $R_5$ is, independently, selected from the group consisting of hydrogen, halogen, and substituted or unsubstituted $C_{1-3}$alkoxy. In some embodiments, each of $R_1$, $R_2$, $R_3$, $R_4$, and $R_5$ is, independently, hydrogen or unsubstituted $C_{1-3}$alkoxy. In some embodiments, each of $R_1$, $R_2$, $R_3$, $R^4$, and $R_5$ is, independently, hydrogen or —$OCH_3$. In some embodiments, $R_2$ and $R_4$ are —$OCH_3$, and $R_1$, $R_3$, and $R_5$ are hydrogen. In some embodiments, $R_2$ and $R_3$ are —$OCH_3$, and $R_1$, $R_4$, and $R_5$ are hydrogen. In some embodiments, $R_1$ and $R_2$ are —$OCH_3$, and $R_3$, $R^4$, and $R_5$ are hydrogen. In some embodiments, $R_1$ and $R_4$ are —$OCH_3$, and $R_2$, $R_3$, and $R_5$ are hydrogen.

In any of these embodiments, each of $R_7$, $R_8$, $R_9$, and $R_{12}$ is, independently, selected from the group consisting of hydrogen, halogen, hydroxyl, cyano, and nitro. In some embodiments, each of $R_7$, $R_8$, $R_9$, and $R_{12}$ is, independently, selected from the group consisting of hydrogen, halogen, and hydroxyl. In some embodiments, each of $R_7$, $R_8$, $R_9$, and $R_{12}$ is, independently, hydrogen or halogen.

In some embodiments, each of $R_1$, $R_2$, $R_3$, $R_4$, and $R_5$ is, independently, selected from the group consisting of hydrogen, halogen, hydroxyl, cyano, nitro, substituted or unsubstituted alkyl, substituted or unsubstituted alkoxy, substituted or unsubstituted amine; and each of $R_7$, $R_8$, $R_9$, and $R_{12}$ is, independently, selected from the group consisting of hydrogen, halogen, hydroxyl, cyano, and nitro.

In some embodiments, each of $R_1$, $R_2$, $R_3$, $R_4$, and $R_5$ is, independently, selected from the group consisting of hydrogen, halogen, and substituted or unsubstituted $C_{1-3}$alkoxy; and each of $R_7$, $R_8$, $R_9$, and $R_{12}$ is, independently, selected from the group consisting of hydrogen, halogen, and hydroxyl.

In some embodiments, each of $R_1$, $R_2$, $R_3$, $R^4$, and $R_5$ is, independently, hydrogen or unsubstituted $C_{1-3}$alkoxy; and each of $R_7$, $R_8$, $R_9$, and $R_{12}$ is, independently, hydrogen or halogen.

In some embodiments, each of $R_1$, $R_2$, $R_3$, $R_4$, and $R_5$ is, independently, hydrogen or —$OCH_3$; and each of $R_7$, $R_8$, $R_9$, and $R_{12}$ is, independently, hydrogen or halogen. In some embodiments, $R_2$ and $R^4$ are —$OCH_3$, and $R_1$, $R_3$, and $R_5$ are hydrogen. In some embodiments, $R_2$ and $R_3$ are —$OCH_3$, and $R_1$, $R_4$, and $R_5$ are hydrogen. In some embodiments, $R_1$ and $R_2$ are —$OCH_3$, and $R_3$, $R_4$, and $R_5$ are hydrogen. In some embodiments, $R_1$ and $R^4$ are —$OCH_3$, and $R_2$, $R_3$, and $R_5$ are hydrogen.

In some embodiments, the compound is

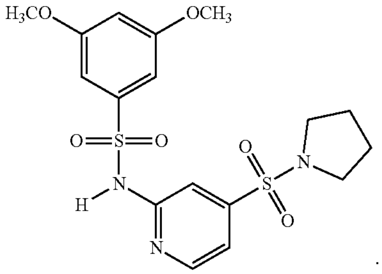 [SMILES: COc1cc(OC)cc(S(=O)(=O)Nc2cc(S(=O)(=O)N3CCCC3)ccn2)c1]

The present disclosure also provides pharmaceutical compositions comprising any one or more of the compounds of Formula I described herein, or pharmaceutically acceptable salts thereof, and a pharmaceutically acceptable carrier. In some embodiments, the pharmaceutical composition is an oral formulation, an intravenous formulation, a topical formulation, an intraperitoneal formulation, an intrapleural formulation, an intravesical formulation, or an intrathecal formulation. In some embodiments, the oral formulation is a pill, tablet, capsule, cachet, gel-cap, pellet, powder, granule, or liquid. In some embodiments, the oral formulation is a pill, tablet, capsule, gel-cap, or liquid.

In some embodiments, the pharmaceutical composition further comprises an anti-cancer agent. As used herein, the phrase “anti-cancer agent” is meant to include all forms of treatment of cancer including, but not limited to, traditional chemotherapy (i.e., chemotherapeutic agents, whether they are administered parenterally or orally), immunotherapeutic agents, small molecule enzyme or kinase inhibitors, intravesical therapeutic agents, antibody inhibitors of receptors or kinases, antibody-drug conjugates, and radiation therapy.

Examples of chemotherapeutic agents include, but are not limited to, cisplatin, carboplatin, oxaliplatin, nedaplatin, triplatin tetranitrate, phenanthriplatin, picoplatin, satraplatin, methotrexate, vincristine, doxorubicin, tunicamycin, oligomycin, bortezomib, MG132, 5-flurouracil, sorafenib, flavopiridol, gemcitabine, taxol, mercaptopurine, thioguanine, hydroxyurea, cytarabine, mitomycin, cyclophosphamide, ifosfamide, nitrosourea, dacarbazine, procarbizine, an etoposide, a campathecin, bleomycin, idarubicin, daunorubicin, dactinomycin, distamycin A, etidium, netropsin, auristatin, amsacrine, prodigiosin, bortexomib, pibenzimol, tomaymycin, duocarmycin SA, plicamycin, mitoxantrone, asparaginase, vinblastine, vinorelbine, paclitaxel, docetaxel. CPT-11, gleevec, erlotinib, gefitinib, ibrutinib, crizotinib, ceritinib, lapatinib, navitoclax, and regorafenib, or any combination thereof. In some embodiments, the chemotherapeutic agent is a combination of agents, such as, for example, methotrexate/vincristine/doxorubicin/cisplatin (MVAC) or gemcitabine/cisplatin.

Examples of immunotherapeutic agents include, but are not limited to, OPDIVO® (nivolumab), KEYTRUDA® (pembrolizumab), TECENTRIQ® (atezolizumab), IMFINZI® (durvalumab), YERVOY® (ipilumumab), ERBITUX® (cetuximab), AVASTIN® (bevacizumab), HERCEPTIN® (trastuzumab), PERJETA® (pertuzumab), VECTIBIX® (panitumumab), PORTRAZZA™ (necitumumab), UNITUXIN™ (dinutuximab), CIRAMZA® (ramucirumab), LARTRUVO® (olaratumab), KADCYLA® (ado-trastuzumab emtansineb), XGEVA® (denosumab), and BAVENCIO® (avelumab), or any combination thereof. In some embodiments. the immunotherapeutic agent is nivolumab, pembrolizumab, atezolizumab, durvalab, ipilumumab, cetuximab, bevacizumab, trastuzumab, pertuzumab, panitumumab, necitumumab, dinutuximab, ramucirumab, olaratumab, ado-trastuzumab emtansineb, denosumab, or avelumab, or any combination thereof. In some embodiments, the immunotherapeutic agent is nivolumab, pembrolizumab, atezolizumab, durvalab, ipilumumab, cetuximab, bevacizumab, or trastuzumab, or any combination thereof.

In some embodiments, the immunotherapeutic agents include immune checkpoint inhibitors. Examples of immune checkpoint inhibitors include, but are not limited to, YERVOY® (Ipilimumab), tremelimumab, MGA271, MGA271, indoximod, INCB024360, BMS-986016, or any combination thereof.

In some embodiments, the immunotherapeutic agents include PD-1 and/or PD-L1 inhibitors. Examples of PD-1 and PD-L1 inhibitors include but are not limited to OPDIVO® (nivolumab), KEYTRUDA® (pembrolizumab), TECENTRIQ® (atezolizumab), BAVENCIO® (avelumab), IMFINZI® (durvalumab), LIBTAYO® (cemiplimab) JTX-4014, spartalizumab, camrelizumab, sintilimab, tislelizumab, toripalimab, dostarlimab, pidilizumab, INCMGA00012, AMP-224, AMP-514, KN035, CK-301, AUNP12, CA-170, and BMS986189, or any combination thereof.

In some embodiments, the ratio of the compound having Formula I to the anti-cancer agent in the pharmaceutical composition is from about 0.01:1 to about 100:1 w/w.

The pharmaceutical compositions described herein can be administered to a patient in need thereof in an oral formulation, an intravenous formulation, a topical formulation, an intraperitoneal formulation, an intrapleural formulation, an intravesical formulation, or an intrathecal formulation. The compositions may be formulated in a suitable controlled-release vehicle, with an adjuvant, or as a depot formulation.

In some embodiments, the carrier is a pharmaceutically acceptable carrier. Pharmaceutically acceptable carriers include, but are not limited to, aqueous vehicles such as water, alcohol (e.g., ethanol or glycol), saline solutions, dextrose solutions, and balanced salt solutions, as well as nonaqueous vehicles such as alcohols and oils, including plant or vegetable-derived oils such as olive oil, cottonseed oil, corn oil, canola oil, sesame oil, and other non-toxic oils. The compositions may also comprise one or more pharmaceutically acceptable excipients.

The compositions may be formulated for administration to a subject in any suitable dosage form. The compositions may be formulated for oral, buccal, nasal, transdermal, parenteral, injectable, intravenous, subcutaneous, intramuscular, rectal, or vaginal administration. The compositions may be formulated in a suitable controlled-release vehicle, with an adjuvant, or as a depot formulation.

Preparations for parenteral administration include, but are not limited to, sterile solutions ready for injection, sterile dry soluble products ready to be combined with a solvent just prior to use, including, but not limited to, hypodermic tablets, sterile suspensions ready for injection, sterile dry insoluble products ready to be combined with a vehicle just prior to use and sterile emulsions.

Solid dosage forms include, but are not limited to, tablets, pills, powders, bulk powders, capsules, granules, and combinations thereof. Solid dosage forms may be prepared as compressed, chewable lozenges and tablets which may be enteric-coated, sugar coated or film-coated. Solid dosage forms may be hard or encased in soft gelatin, and granules and powders may be provided in non-effervescent or effervescent form. Solid dosage forms may be prepared for dissolution or suspension in a liquid or semi-liquid vehicle prior to administration. Solid dosage forms may be prepared for immediate release, controlled release, or any combination thereof. Controlled release includes, but is not limited to, delayed release, sustained release, timed pulsatile release, and location-specific pulsatile release, and combinations thereof.

Liquid dosage forms include, but are not limited to, aqueous solutions, emulsions, suspensions, solutions and/or suspensions reconstituted from non-effervescent granules and effervescent preparations reconstituted from effervescent granules. Aqueous solutions include, but are not limited to, elixirs and syrups. Emulsions may be oil-in water or water-in-oil emulsions.

Pharmaceutically acceptable excipients utilized in solid dosage forms include, but are not limited to, coatings, binders, lubricants, diluents, disintegrating agents, coloring agents, flavoring agents, preservatives, sweeteners, and wetting agents. Enteric-coated tablets, due to their enteric-coating, resist the action of stomach acid and dissolve or disintegrate in the neutral or alkaline intestines. Other examples of coatings include, but are not limited to, sugar coatings and polymer coatings. Sweetening agents are useful in the formation of chewable tablets and lozenges. Pharmaceutically acceptable excipients used in liquid dosage forms include, but are not limited to, solvents, suspending agents, dispersing agents, emulsifying agents, surfactants, emollients, coloring agents, flavoring agents, preservatives, and sweeteners.

Suitable examples of binders include, but are not limited to, glucose solution, acacia mucilage, gelatin solution, sucrose and starch paste. Suitable examples of lubricants include, but are not limited to, talc, starch, magnesium or calcium stearate, lycopodium and stearic acid. Suitable examples of diluents include, but are not limited to, lactose, sucrose, starch, kaolin, salt, mannitol and dicalcium phosphate. Suitable examples of disintegrating agents include, but are not limited to, corn starch, potato starch, bentonite, methylcellulose, agar and carboxymethylcellulose. Suitable examples of emulsifying agents include, but are not limited to, gelatin, acacia, tragacanth, bentonite, and surfactants such as polyoxyethylene sorbitan monooleate. Suitable examples of suspending agents include, but are not limited to, sodium carboxymethylcellulose, pectin, tragacanth, veegum and acacia.

Suitable examples of coloring agents include, but are not limited to, any of the approved certified water soluble FD and C dyes, mixtures thereof, and water insoluble FD and D dyes suspended on alumina hydrate. Suitable examples of sweetening agents include, but are not limited to, dextrose, sucrose, fructose, lactose, mannitol and artificial sweetening agents such as saccharin, aspartame, sucralose, acelsulfame potassium, and other artificial sweeteners. Suitable examples of flavoring agents include, but are not limited to, synthetic flavors and natural flavors extracted from plants such as fruits and mints, and synthetic blends of compounds which produce a pleasant sensation. Suitable examples of wetting agents include, but are not limited to, propylene glycol monostearate, sorbitan monooleate, diethylene glycol monolaurate and polyoxyethylene laural ether. Suitable examples of enteric-coatings include, but are not limited to, fatty acids, fats, waxes, shellac, ammoniated shellac and cellulose acetate phthalates. Suitable examples of film coatings include, but are not limited to, hydroxyethylcellulose, sodium carboxymethylcellulose, polyethylene glycol 4000 and cellulose acetate phthalate. Suitable examples of preservatives include, but are not limited to, glycerin, methyl and propylparaben, ethylparaben, butylparaben, isobutylparaben, isopropylparaben, benzylparaben, citrate, benzoic acid, sodium benzoate and alcohol.

Suitable examples of elixirs include, but are not limited to, clear, sweetened, hydroalcoholic preparations. Pharmaceutically acceptable carriers used in elixirs include solvents. Suitable examples of syrups include, but are not limited to, concentrated aqueous solutions of a sugar, for example, sucrose, and may contain a preservative. An emulsion is a two-phase system in which one liquid is dispersed throughout another liquid. Pharmaceutically acceptable carriers used in emulsions can also include emulsifying agents and preservatives. Suspensions may use pharmaceutically acceptable suspending agents and preservatives. Pharmaceutically acceptable substances used in non-effervescent granules, to be reconstituted into a liquid oral dosage form, include, but are not limited to, diluents, sweeteners, and wetting agents. Pharmaceutically acceptable substances used in effervescent granules, to be reconstituted into a liquid oral dosage form, include, but are not limited to, organic acids and a source of carbon dioxide. Sources of carbon dioxide include, but are not limited to, sodium bicarbonate and sodium carbonate. Coloring and flavoring agents may be used in all such dosage forms.

Additional excipients that may be included in any dosage forms include, but are not limited to, antimicrobial agents, isotonic agents, buffers, antioxidants, local anesthetic agents, sequestering or chelating agents, analgesic agents, antiemetic agents, and other agents to enhance selected characteristics of the formulation.

Antimicrobial agents may be cidal or static, and may be antimicrobial, antifungal, antiparasitic, or antiviral. Suitable examples of commonly used antimicrobial agents include, but are not limited to, phenols or cresols, mercurials, benzyl alcohol, chlorobutanol, methyl and propyl p-hydroxy benzoic acid esters, thimerosal, benzalkonium chloride and benzethonium chloride. Acidic or basic pH may be used for antimicrobial effects in some aspects. Suitable examples of isotonic agents include, but are not limited to, sodium chloride and dextrose. Suitable examples of buffers include, but are not limited to, phosphate and citrate buffers. A non-limiting example of a chelating agent for metal ions is EDTA.

The present disclosure also provides methods of treating a mammal having cancer comprising administering to the mammal in need thereof a compound having Formula I:

(I)

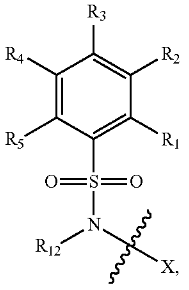

or a pharmaceutically acceptable salt thereof, wherein:

X is

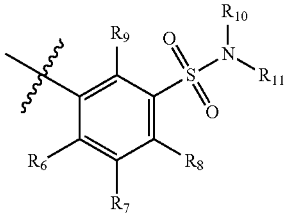

or

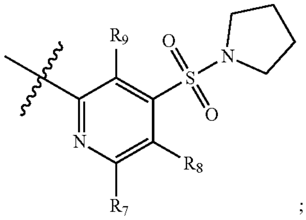

;

each of $R_1$, $R_2$, $R_3$, $R_4$, and $R_5$ is, independently, selected from the group consisting of hydrogen, halogen, hydroxyl, cyano, nitro, substituted or unsubstituted alkyl, substituted or unsubstituted alkenyl, substituted or unsubstituted alkoxy, substituted or unsubstituted amine, substituted or unsubstituted alkylamino, substituted or unsubstituted aminoalkoxy, and substituted or unsubstituted alkylthio;

$R_6$ is selected from the group consisting of hydrogen, halogen, hydroxyl, cyano, nitro, substituted or unsubstituted alkyl, substituted or unsubstituted alkoxy, substituted or unsubstituted amine, substituted or unsubstituted alkylamino, and substituted or unsubstituted aminoalkoxy;

each of $R_7$, $R_8$, $R_9$, and $R_{12}$ is, independently, selected from the group consisting of hydrogen, halogen, hydroxyl, cyano, nitro, substituted or unsubstituted alkyl, substituted or unsubstituted alkoxy, and substituted or unsubstituted amine; and $R_{10}$ and $R_{11}$ are, independently, selected from the group consisting of hydrogen, substituted or unsubstituted alkyl, and substituted or unsubstituted cycloalkyl, or together with the nitrogen to which they are bonded form a substituted or unsubstituted heteroaryl or a substituted or unsubstituted heterocycloalkyl;

wherein the cancer is selected from the group consisting of melanoma, prostate cancer, pancreatic cancer, breast cancer, colon and rectal cancer, lung cancer, ovarian cancer, endometrial cancer, cervical cancer, esophageal cancer, stomach cancer, thyroid cancer, kidney cancer, liver cancer, mesothelioma, skin cancer, and brain cancer, such as glioblastoma. In addition, the cancer can be selected from a leukemia, a lymphoma, a myeloma (such as multiple myeloma), and a myelodysplastic neoplasm/myeloproferative disease.

In some embodiments, X is

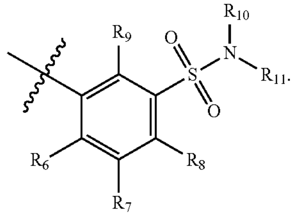

In some embodiments, each of $R_1$, $R_2$, $R_3$, $R_4$, and $R_5$ is, independently, selected from the group consisting of hydrogen, halogen, hydroxyl, cyano, nitro, substituted or unsubstituted alkyl, substituted or unsubstituted alkoxy, substituted or unsubstituted amine. In some embodiments, each of $R_1$, $R_2$, $R_3$, $R_4$, and $R_5$ is, independently, selected from the group consisting of hydrogen, halogen, hydroxyl, nitro, substituted or unsubstituted $C_{1-3}$alkyl, and substituted or unsubstituted $C_{1-3}$alkoxy. In some embodiments, each of $R_1$, $R_2$, $R_3$, $R_4$, and $R_5$ is, independently, selected from the group consisting of hydrogen, halogen, and substituted or unsubstituted $C_{1-3}$alkoxy. In some embodiments, each of $R_1$, $R_2$, $R_3$, $R_4$, and $R_5$ is, independently, hydrogen or unsubstituted $C_{1-3}$alkoxy. In some embodiments, each of $R_1$, $R_2$, $R_3$, $R_4$, and $R_5$ is, independently, hydrogen or $—OCH_3$. In some embodiments, $R_2$ and $R_4$ are $—OCH_3$, and $R_1$, $R_3$, and $R_5$ are hydrogen. In some embodiments, $R_2$ and $R_3$ are $—OCH_3$, and $R_1$, $R_4$, and $R_5$ are hydrogen. In some embodiments, $R_1$ and $R_2$ are $—OCH_3$, and $R_3$, $R^4$, and $R_5$ are hydrogen. In some embodiments, $R_1$ and $R_4$ are $—OCH_3$, and $R_2$, $R_3$, and $R_5$ are hydrogen.

In any of these embodiments, $R_6$ is selected from the group consisting of hydrogen, halogen, hydroxyl, nitro, substituted or unsubstituted alkyl, and substituted or unsubstituted alkoxy. In some embodiments, $R_6$ is selected from the group consisting of hydrogen, halogen, substituted or unsubstituted $C_{1-4}$alkyl, and substituted or unsubstituted $C_{1-4}$alkoxy. In some embodiments, $R_6$ is selected from the group consisting of hydrogen, unsubstituted $C_{1-3}$alkyl, and unsubstituted $C_{1-3}$alkoxy. In some embodiments, $R_6$ is selected from the group consisting of hydrogen, methyl, methoxy, ethoxy, $—OCH(CH_3)_2$.

In any of these embodiments, each of $R_7$, $R_8$, $R_9$, and $R_{12}$ is, independently, selected from the group consisting of hydrogen, halogen, hydroxyl, cyano, and nitro. In some embodiments, each of $R_7$, $R_8$, $R_9$, and $R_{12}$ is, independently, selected from the group consisting of hydrogen, halogen, and hydroxyl. In some embodiments, each of $R_7$, $R_8$, $R_9$, and $R_{12}$ is, independently, hydrogen or halogen.

In any of these embodiments, $R_{10}$ and $R_{11}$ are, independently, selected from the group consisting of hydrogen, substituted or unsubstituted alkyl, and substituted or unsubstituted cycloalkyl, or together with the nitrogen to which they are bonded form a substituted or unsubstituted heterocycloalkyl. In some embodiments, $R_{10}$ and $R_{11}$ are, independently, selected from the group consisting of hydrogen, unsubstituted $C_{1-4}$alkyl, and unsubstituted cycloalkyl, or together with the nitrogen to which they are bonded form an unsubstituted heterocycloalkyl. In some embodiments, $R_{10}$ and $R_{11}$ are, independently, selected from the group consisting of hydrogen, ethyl, or $—C(CH_3)_3$, or together with the nitrogen to which they are bonded form piperidine or pyrrolidine.

In some embodiments, each of $R_1$, $R_2$, $R_3$, $R^4$, and $R_5$ is, independently, selected from the group consisting of hydrogen, halogen, hydroxyl, cyano, nitro, substituted or unsubstituted alkyl, substituted or unsubstituted alkoxy, substituted or unsubstituted amine; $R_6$ is selected from the group consisting of hydrogen, halogen, hydroxyl, nitro, substituted or unsubstituted alkyl, and substituted or unsubstituted alkoxy; each of $R_7$, $R_8$, $R_9$, and $R_{12}$ is, independently, selected from the group consisting of hydrogen, halogen, hydroxyl, cyano, and nitro; and $R_{10}$ and $R_{11}$ are, independently, selected from the group consisting of hydrogen, substituted or unsubstituted alkyl, and substituted or unsubstituted cycloalkyl, or together with the nitrogen to which they are bonded form a substituted or unsubstituted heterocycloalkyl.

In some embodiments, each of $R_1$, $R_2$, $R_3$, $R^4$, and $R_5$ is, independently, selected from the group consisting of hydrogen, halogen, hydroxyl, nitro, substituted or unsubstituted $C_{1-3}$alkyl, and substituted or unsubstituted $C_{1-3}$alkoxy; $R_6$ is selected from the group consisting of hydrogen, halogen, substituted or unsubstituted $C_{1-4}$alkyl, and substituted or unsubstituted $C_{1-4}$alkoxy; each of $R_7$, $R_8$, $R_9$, and $R_{12}$ is, independently, selected from the group consisting of hydrogen, halogen, and hydroxyl; and $R_{10}$ and $R_{11}$ are, independently, selected from the group consisting of hydrogen, unsubstituted $C_{1-4}$alkyl, and unsubstituted cycloalkyl, or together with the nitrogen to which they are bonded form an unsubstituted heterocycloalkyl.

In some embodiments, each of $R_1$, $R_2$, $R_3$, $R_4$, and $R_5$ is, independently, selected from the group consisting of hydrogen, halogen, and substituted or unsubstituted $C_{1-3}$alkoxy; $R_6$ is selected from the group consisting of hydrogen, unsubstituted $C_{1-3}$alkyl, and unsubstituted $C_{1-3}$alkoxy; each of $R_7$, $R_8$, $R_9$, and $R_{12}$ is, independently, hydrogen or halogen; and $R_{10}$ and $R_{11}$ are, independently, selected from the group consisting of hydrogen, ethyl, or $—C(CH_3)_3$, or together with the nitrogen to which they are bonded form piperidine or pyrrolidine.

In some embodiments, each of $R_1$, $R_2$, $R_3$, $R^4$, and $R_5$ is, independently, hydrogen or unsubstituted $C_{1-3}$alkoxy; $R_6$ is selected from the group consisting of hydrogen, methyl, methoxy, ethoxy, $—OCH(CH_3)_2$; each of $R_7$, $R_8$, $R_9$, and $R_{12}$ is, independently, hydrogen or halogen; and $R_{10}$ and $R_{11}$ are, independently, selected from the group consisting of hydrogen, ethyl, or $—C(CH_3)_3$, or together with the nitrogen to which they are bonded form piperidine or pyrrolidine.

In some embodiments, each of $R_1$, $R_2$, $R_3$, $R_4$, and $R_5$ is, independently, hydrogen or $—OCH_3$; $R_6$ is selected from the group consisting of hydrogen, methyl, methoxy, ethoxy, $—OCH(CH_3)_2$; each of $R_7$, $R_8$, $R_9$, and $R_{12}$ is, independently, hydrogen or halogen; and $R_{10}$ and $R_{11}$ are, independently, selected from the group consisting of hydrogen, ethyl, or $—C(CH_3)_3$, or together with the nitrogen to which they are bonded form piperidine or pyrrolidine. In some embodiments, $R_2$ and $R_4$ are $—OCH_3$, and $R_1$, $R_3$, and $R_5$ are hydrogen. In some embodiments, $R_2$ and $R_3$ are $—OCH_3$, and $R_1$, $R_4$, and $R_5$ are hydrogen. In some embodiments, $R_1$ and $R_2$ are $—OCH_3$, and $R_3$, $R_4$, and $R_5$ are hydrogen. In some embodiments, $R_1$ and $R_4$ are $—OCH_3$, and $R_2$, $R_3$, and $R_5$ are hydrogen.

In some embodiments, the compound is selected from the group consisting of
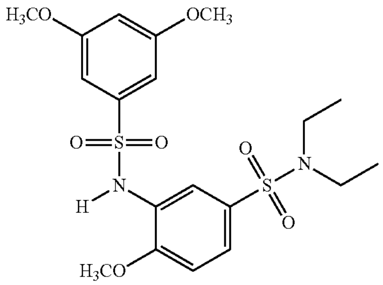,
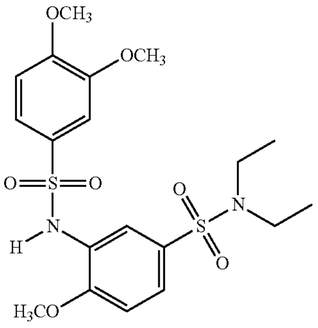,
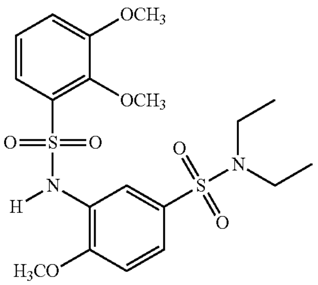,
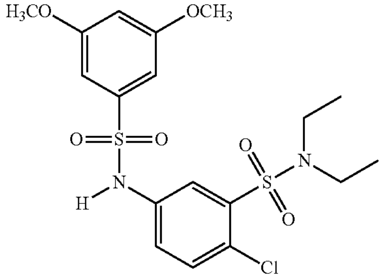,
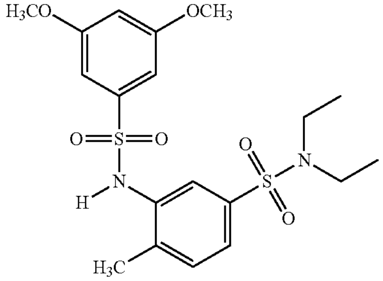,
-continued
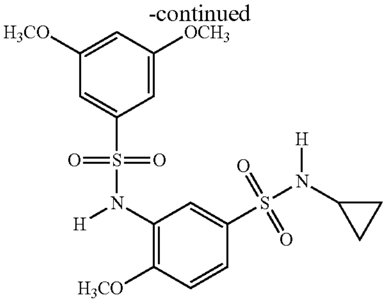,
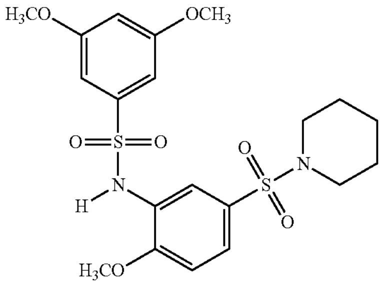,
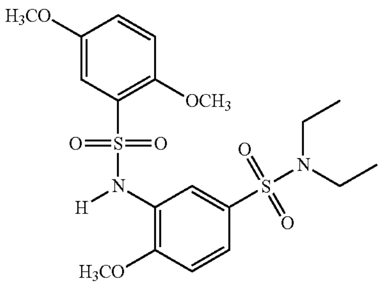,
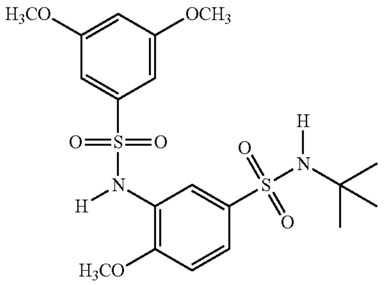,
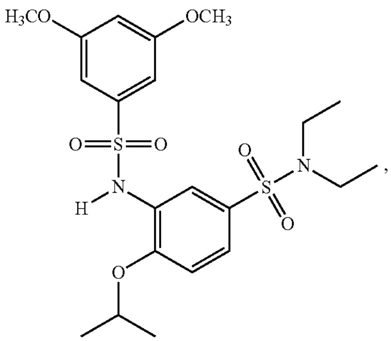, and -continued

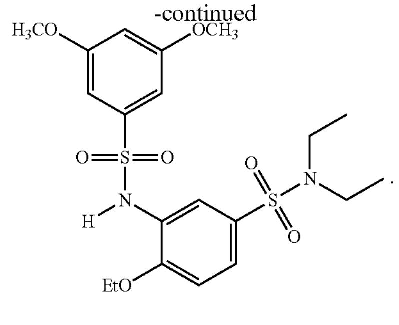

In some embodiments, X is

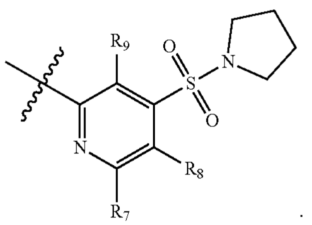

In some embodiments, each of $R_1$, $R_2$, $R_3$, $R_4$, and $R_5$ is, independently, selected from the group consisting of hydrogen, halogen, hydroxyl, cyano, nitro, substituted or unsubstituted alkyl, substituted or unsubstituted alkoxy, substituted or unsubstituted amine. In some embodiments, each of $R_1$, $R_2$, $R_3$, $R^4$, and $R_5$ is, independently, selected from the group consisting of hydrogen, halogen, hydroxyl, nitro, substituted or unsubstituted $C_{1-3}$alkyl, and substituted or unsubstituted $C_{1-3}$alkoxy. In some embodiments, each of $R_1$, $R_2$, $R_3$, $R_4$, and $R_5$ is, independently, selected from the group consisting of hydrogen, halogen, and substituted or unsubstituted $C_{1-3}$alkoxy. In some embodiments, each of $R_1$, $R_2$, $R_3$, $R_4$, and $R_5$ is, independently, hydrogen or unsubstituted $C_{1-3}$alkoxy. In some embodiments, each of $R_1$, $R_2$, $R_3$, $R^4$, and $R_5$ is, independently, hydrogen or —$OCH_3$. In some embodiments, $R_2$ and $R_4$ are —$OCH_3$, and $R_1$, $R_3$, and $R_5$ are hydrogen. In some embodiments, $R_2$ and $R_3$ are —$OCH_3$, and $R_1$, $R_4$, and $R_5$ are hydrogen. In some embodiments, $R_1$ and $R_2$ are —$OCH_3$, and $R_3$, $R^4$, and $R_5$ are hydrogen. In some embodiments, $R_1$ and $R_4$ are —$OCH_3$, and $R_2$, $R_3$, and $R_5$ are hydrogen.

In any of these embodiments, each of $R_7$, $R_8$, $R_9$, and $R_{12}$ is, independently, selected from the group consisting of hydrogen, halogen, hydroxyl, cyano, and nitro. In some embodiments, each of $R_7$, $R_8$, $R_9$, and $R_{12}$ is, independently, selected from the group consisting of hydrogen, halogen, and hydroxyl. In some embodiments, each of $R_7$, $R_8$, $R_9$, and $R_{12}$ is, independently, hydrogen or halogen.

In some embodiments, each of $R_1$, $R_2$, $R_3$, $R^4$, and $R_5$ is, independently, selected from the group consisting of hydrogen, halogen, hydroxyl, cyano, nitro, substituted or unsubstituted alkyl, substituted or unsubstituted alkoxy, substituted or unsubstituted amine; and each of $R_7$, $R_8$, $R_9$, and $R_{12}$ is, independently, selected from the group consisting of hydrogen, halogen, hydroxyl, cyano, and nitro.

In some embodiments, each of $R_1$, $R_2$, $R_3$, $R_4$, and $R_5$ is, independently, selected from the group consisting of hydrogen, halogen, and substituted or unsubstituted $C_{1-3}$alkoxy; and each of $R_7$, $R_8$, $R_9$, and $R_{12}$ is, independently, selected from the group consisting of hydrogen, halogen, and hydroxyl.

In some embodiments, each of $R_1$, $R_2$, $R_3$, $R^4$, and $R_5$ is, independently, hydrogen or unsubstituted $C_{1-3}$alkoxy; and each of $R_7$, $R_8$, $R_9$, and $R_{12}$ is, independently, hydrogen or halogen.

In some embodiments, each of $R_1$, $R_2$, $R_3$, $R^4$, and $R_5$ is, independently, hydrogen or —$OCH_3$; and each of $R_7$, $R_8$, $R_9$, and $R_{12}$ is, independently, hydrogen or halogen. In some embodiments, $R_2$ and $R^4$ are —$OCH_3$, and $R_1$, $R_3$, and $R_5$ are hydrogen. In some embodiments, $R_2$ and $R_5$ are —$OCH_3$, and $R_1$, $R_4$, and $R_5$ are hydrogen. In some embodiments, $R_1$ and $R_2$ are —$OCH_3$, and $R_3$, $R_4$, and $R_5$ are hydrogen. In some embodiments, $R_1$ and $R^4$ are —$OCH_3$, and $R_2$, $R_3$, and $R_5$ are hydrogen.

In some embodiments, the compound is

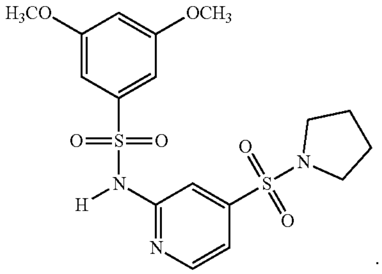 [SMILES: COc1cc(OC)cc(S(=O)(=O)Nc2cc(S(=O)(=O)N3CCCC3)ccn2)c1]

The amount of the compound having Formula I to be administered may be that amount which is therapeutically effective. The dosage to be administered may depend on the characteristics of the subject being treated, e.g., the particular animal treated, age, weight, health, types of concurrent treatment, if any, and frequency of treatments, and on the nature and extent of the cancer, and can be easily determined by one skilled in the art (e.g., by the clinician). The selection of the specific dose regimen can be selected or adjusted or titrated by the clinician according to methods known to the clinician to obtain the desired clinical response. In addition, in vitro or in vivo assays may optionally be employed to help identify optimal dosage ranges. The precise dose to be employed in the compositions may also depend on the route of administration, and should be decided according to the judgment of the practitioner and each patient's circumstances.

The compositions may be prepared to provide from about 0.05 mg to about 500 mg of the compound having Formula I, or pharmaceutically acceptable salt thereof. In some embodiments, the compositions may comprise from about 1 mg to about 200 mg, from about 10 mg to about 200 mg, from about 10 mg to about 100 mg, from about 50 mg to about 100 mg, from about 20 mg to about 400 mg, from about 100 mg to about 300 mg, or from about 50 mg to about 250 mg of the compound of Formula I, or an isomer, tautomer, or solvate thereof, or a pharmaceutically acceptable salt thereof.

Suitable dosage ranges for oral administration include, but are not limited to, from about 0.001 mg/kg body weight to about 200 mg/kg body weight, from about 0.01 mg/kg body weight to about 100 mg/kg body weight, from about 0.01 mg/kg body weight to about 70 mg/kg body weight, from about 0.1 mg/kg body weight to about 50 mg/kg body weight, from 0.5 mg/kg body weight to about 20 mg/kg body weight, or from about 1 mg/kg body weight to about 10 mg/kg body weight. In some embodiments, the oral dose is about 5 mg/kg body weight.

Suitable dosage ranges for intravenous administration include, but are not limited to, from about 0.01 mg/kg body weight to about 500 mg/kg body weight, from about 0.1 mg/kg body weight to about 100 mg/kg body weight, from about 1 mg/kg body weight to about 50 mg/kg body weight, or from about 10 mg/kg body weight to about 35 mg/kg body weight.

Suitable dosage ranges for other routes of administration can be calculated based on the forgoing dosages as known by one skilled in the art. For example, recommended dosages for intradermal, intramuscular, intraperitoneal, subcutaneous, epidural, sublingual, intracerebral, transdermal, or inhalation are in the range from about 0.001 mg/kg body weight to about 200 mg/kg body weight, from about 0.01 mg/kg body weight to about 100 mg/kg body weight, from about 0.1 mg/kg body weight to about 50 mg/kg body weight, or from about 1 mg/kg body weight to about 20 mg/kg body weight. Effective doses may be extrapolated from dose-response curves derived from in vitro or animal model test systems. Such animal models and systems are well known in the art.

In some embodiments, the amount of the compound administered to the mammal is from about 0.1 mg to about 500 mg, from about 1 mg to about 250 mg, from about 5 mg to about 400 mg, from about 10 mg to about 250 mg, from about 20 mg to about 200 mg, or from about 40 mg to about 100 mg. In some embodiments, the amount of the compound administered to the mammal is from about 0.1 mg to about 500 mg. In some embodiments, the amount of the compound administered to the mammal is from about 1 mg to about 250 mg. In some embodiments, the amount of the compound administered to the mammal is from about 5 mg to about 400 mg. In some embodiments, the amount of the compound administered to the mammal is from about 10 mg to about 250 mg. In some embodiments, the amount of the compound administered to the mammal is from about 20 mg to about 200 mg. In some embodiments, the amount of the compound administered to the mammal is from about 40 mg to about 100 mg.

In some embodiments, the mammal is human.

In some embodiments, the mammal is also administered radiation therapy, a chemotherapeutic agent, an immunotherapeutic agent, a biologic agent, or any combination thereof.

The present disclosure also provides methods for inhibiting genome-wide hypomethylation. Such methods may comprise treatment methods, by which inhibiting genome-wide hypomethylation treats any condition in which genome-wide hypomethylation plays a role, including cancer.

In some embodiments, the methods of treatment further comprise administering another therapy to the subject. In some embodiments, the another therapy is radiation therapy, chemotherapy, immunotherapy, or a combination thereof. In some embodiments, the another therapy is administered to the subject at a lower level compared to the level when administered in the absence of the compound of Formula I.

In some embodiments, the methods comprise contacting a cell with genome-wide hypomethylation with an effective amount of a compound or composition comprising Formula I, or any pharmaceutically acceptable salt thereof. The composition may comprise any dosage form and/or any excipients, including those described or exemplified herein.

In some embodiments, the methods comprise contacting a cancer cell with an effective amount of a compound or composition comprising any of Formula I, or any pharmaceutically acceptable salt thereof. The composition may comprise any dosage form and/or any excipients, including those described or exemplified herein.

In some embodiments, the methods comprise contacting a cell having genome-wide hypomethylation with an effective amount of a compound or composition comprising any of, or any combination thereof, or any pharmaceutically acceptable salt thereof. The composition may comprise any dosage form and/or any excipients, including those described or exemplified herein. In contacting the cell in this manner, the compound or composition inhibits genome-wide hypomethylation. The cell may be within the body of a subject. The cell may be a cancer cell, such as a prostate cancer cell, a breast cancer cell, a kidney cancer cell, an ovarian cancer cell, a lymphoma cell, a melanoma cell, a leukemia cell, or a glioblastoma cell.

In some embodiments, methods for treating a cancer patient comprise administering to the patient a compound or composition comprising any of Formula I, or any combination thereof, or any pharmaceutically acceptable salt thereof, in an amount effective to treat the cancer. In some embodiments, the effective amount is an amount effective to inhibit genome-wide hypomethylation in cancer cells within the patient's body. In some embodiments, the patient is a human cancer patient. In some embodiments, the cancer is associated with genome-wide hypomethylation. The cancer may be any cancer in which genome-wide hypomethylation occurs including, but are not limited to, prostate cancer, breast cancer, kidney cancer, ovarian cancer, lymphoma, leukemia, melanoma, or glioblastoma.

In some embodiments, the cancer is selected from the group consisting of a carcinoma, a sarcoma, a colorectal cancer, a lymphoma, a leukemia, a blastoma, a germ cell cancer, a breast cancer, a lung cancer, a pancreatic cancer, a stomach cancer, a bone cancer, an ovarian cancer, a prostate cancer, a head and neck cancer, a bladder cancer, a cervical cancer, a colon cancer, a skin cancer, a gliobastoma cancer, an esophageal cancer, an oral cancer, a gallbladder cancer, a liver cancer, a testicular cancer, a uterine cancer, a thyroid cancer, and a throat cancer. In some embodiments, the cancer is a colorectal cancer, a head and neck cancer, a pancreatic cancer, a breast cancer, a colon cancer, a lung cancer, or a gliobastoma cancer.

In some embodiments, the cancer is melanoma, prostate cancer, pancreatic cancer, breast cancer, colon cancer, lung cancer, ovarian cancer, or glioblastoma. In some embodiments, the cancer is melanoma. In some embodiments, the cancer is prostate cancer. In some embodiments, the cancer is pancreatic cancer. In some embodiments, the cancer is breast cancer. In some embodiments, the cancer is colon cancer. In some embodiments, the cancer is lung cancer. In some embodiments, the cancer is ovarian cancer. In some embodiments, the cancer is glioblastoma.

Administration may be according to any technique or route suitable to the cancer being treated or the patient's needs. Administration may be, for example, oral, parenteral, or via direct injection. Administration may be directly to the tumor or to a location proximal to the tumor. Delivery may be via the bloodstream. Delivery may include active targeting, for example, by conjugating the compound to an antibody that binds to an antigen on the tumor being treated. Delivery may also be passive.

The present disclosure also provides uses of any one or more of these compounds, or a pharmaceutically acceptable salt thereof, or a composition comprising any one or more of these compounds, or a pharmaceutically acceptable salt thereof, for treating a mammal having cancer.

The present disclosure also provides uses of any one or more of these compounds, or a pharmaceutically acceptable salt thereof, or a composition comprising any one or more of these compounds, or a pharmaceutically acceptable salt thereof, in the preparation of a medicament for treating a mammal having cancer.

In order that the subject matter disclosed herein may be more efficiently understood, examples are provided below. It should be understood that these examples are for illustrative purposes only and are not to be construed as limiting the claimed subject matter in any manner.

EXAMPLES

Example 1: TET-TDG Demethylation in a Subset of Metastatic Melanomas Characterized by Prominent DNA Hypomethylation The TCGA SKCM Infinium 450K methylation array data was mined, and 1,028 CpG sites that are candidate targets of TDG-mediated DNA demethylation in metastatic melanoma were identified. These CpG sites divided metastatic melanomas in two dominant clusters, with the "burgundy" cluster showing prominent genome hypomethylation as opposed to the "green" cluster that had less hypomethylation (data not shown). Remarkably, not only TDG, but also TET1-3 mRNA expression levels were higher in the burgundy cluster enriched for hypomethylated sites (FIG. 1), suggesting activation of both TET and TDG promotes DNA demethylation in this cluster of metastatic SKCM. Importantly, these hypomethylated CpG sites are enriched for melanoma enhancers (Fontanals-Cirera et al., Mol. Cell, 2017, 68, 731-744) (permutation test p-values=0.0229). Pathway analysis of nearby genes revealed enrichment of GO terms of cell proliferation, transcriptional dysregulation in cancer, kinase activity, RAS signaling. EMT, cell motility, and wound healing. Thus, upregulation of the TET-TDG axis leads to hypomethylation of enhancers, promoters and other regulatory elements, leading to transcriptional activation of oncogenes and other genes that ultimately provide a survival/proliferative/invasive advantage to melanoma cells.

Example 2: TET1 and TDG Demethylation in Hypomethylated Lung Cancer

By mining the Infinium 450K methylation array data in the TCGA LC databases LUAD (lung adenocarcinomas) and LUSC (lung squamous cell carcinoma), CpG sites were identified that are candidate targets of TET1-TDG-mediated DNA demethylation. These CpG sites divided LUAD and LUSC cases in two dominant clusters, with the "burgundy" cluster showing prominent genome hypomethylation as opposed to the "green" cluster that had less hypomethylation (data not shown). Thus, approximately a fifth and a seventh of LUSC and LUAD cases, respectively, have a marked signature of TET1-TDG-mediated DNA hypomethylation.

Example 3: TDG Knockdown Partially Corrects the Altered Methylome of Melanoma To assess the possibility that TDG knockdown partially corrects the altered methylome of melanoma, the methylation values in the top and bottom quartile (TDG.High/TDG.Low) of metastatic SKCM were compared for all Illumina 450K probes matching one of the DREAM probes in the SK28 methylome. The results revealed that CpG sites undergoing hypermethylation in TDG knockdown SK28 cells were significantly associated with hypomethylated CpG sites in metastatic SKCM cases with high TDG expression (p-value=1.536e-14 by Fisher's Exact Test).

Example 4: Identification of a First-in-Class TDG Inhibitor, MC1

A virtual screen was carried out using an approach developed previously (Johnson et al., J. Chem. Inf. Model. 2016, 56, 399-411). From the structure of TDG in complex with a 5-carboxylcytosine (5caC)-containing DNA segment (substrate) (Zhang et al., Nat. Chem. Biol., 2012, 8, 328-330), key interactions with drug-like small molecules were recapitulated. This pilot screen used a virtual library of about 15 million compounds, from which the top-scoring 19 computational hits were obtained and characterized them in an enzyme assay (Mancuso et al., Oncogene, 2019, 38, 3710-3728), modified to work on a self-assembled monolayers for matrix-assisted laser desorption/ionization (SAMDI) mass spectrometry platform.

TDG reactions were optimized through assay development to understand the Km of the substrate and enzyme linearity. DMSO tolerance, and assay performance. The final conditions were performed with 10 nM APEL and 5 nM TDG, 200 nM hairpin G:U mismatched substrate (sequence of the substrate: biotinylated CCACTUGTGAAT-TGACAGCCCATGTGCATCAATT CACGAGTGG; SEQ ID NO:1) and 100 nM internal standard (sequence of the standard: biotinylated TTTTT; SEQ ID NO:2)(input sequences) in 1× optimized buffer (1× BER buffer, 1.2 mM $MgCl_2$, 0.01% Bovine Skin Gelatin, 0.6 mM DTT). The reactions were run in 20 μL volume in 384-well polypropylene microplates (Greiner Bio-One) at ambient temperature and quenched by the addition of 100 mM EDTA (final). At defined times, a 2 μL sample of the quenched reactions was then transferred using a 384-channel pipette station to SAMDI 384-biochip arrays functionalized with self-assembled monolayers presenting Neutravidin. The SAMDI arrays were incubated for 1 hour in a humidified chamber to enable immobilization of the substrate, product, and internal standard. The samples were purified by washing the SAMDI biochip arrays with water and dried under compressed air. A matrix comprising 2-hydroxy-5-methoxybenzoic acid in acetonitrile (30 mg/mL) and ascorbic acid in aqueous citrate (500 mM) was applied by dispensing 350 nL of each spot in the array. SAMDI mass spectrometry (MS) was performed using the reflector-negative mode on an AB Sciex TOF/TOF 5800 System, a matrix-assisted laser desorption ionization (MALDI) mass spectrometer (AB Sciex, Framingham, MA). The conversion of substrate to product was calculated by using the ratio of product area under the curve (AUC) divided by the AUC of the internal standard.

Figure 2:
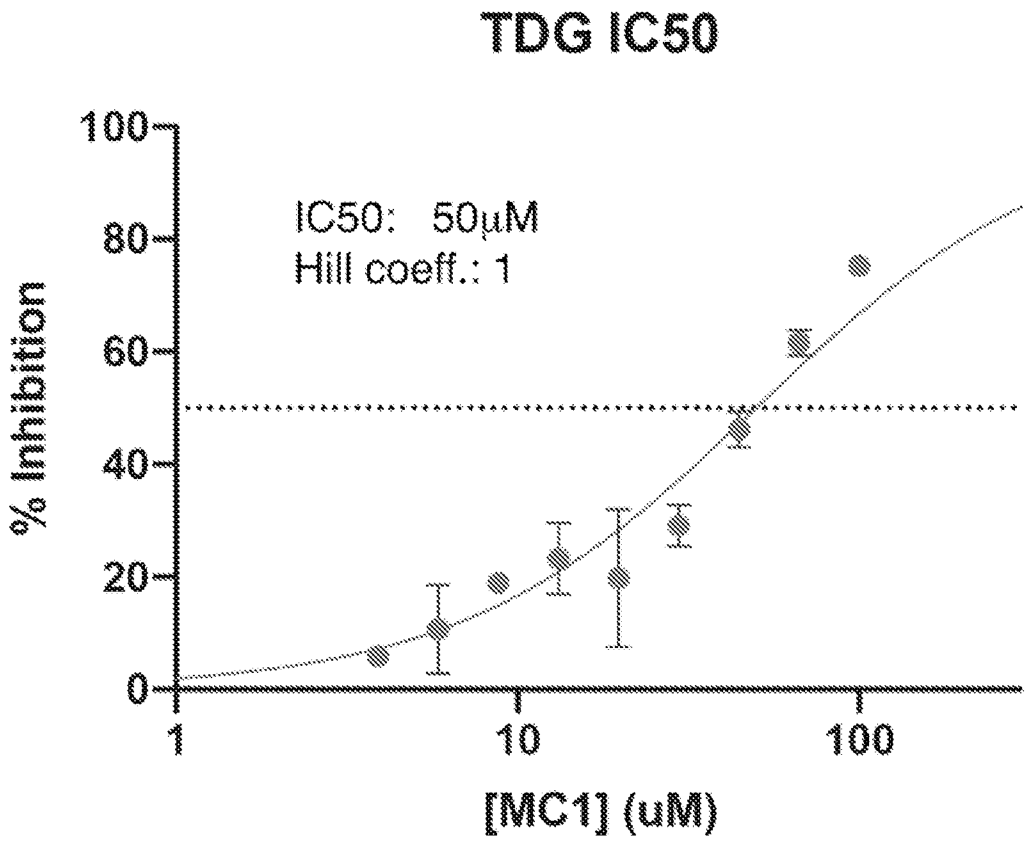
FIG. 2 depicts TDG inhibitory activity of MC1; TDG activity was measured with a hairpin molecular beacon substrate on a SAMDI mass spectrometry platform.

In this assay, a TDG inhibitor, MC1, was identified which had acceptable potency, with an IC50 of 50 μM (see. FIG. 2).

Figure 3:
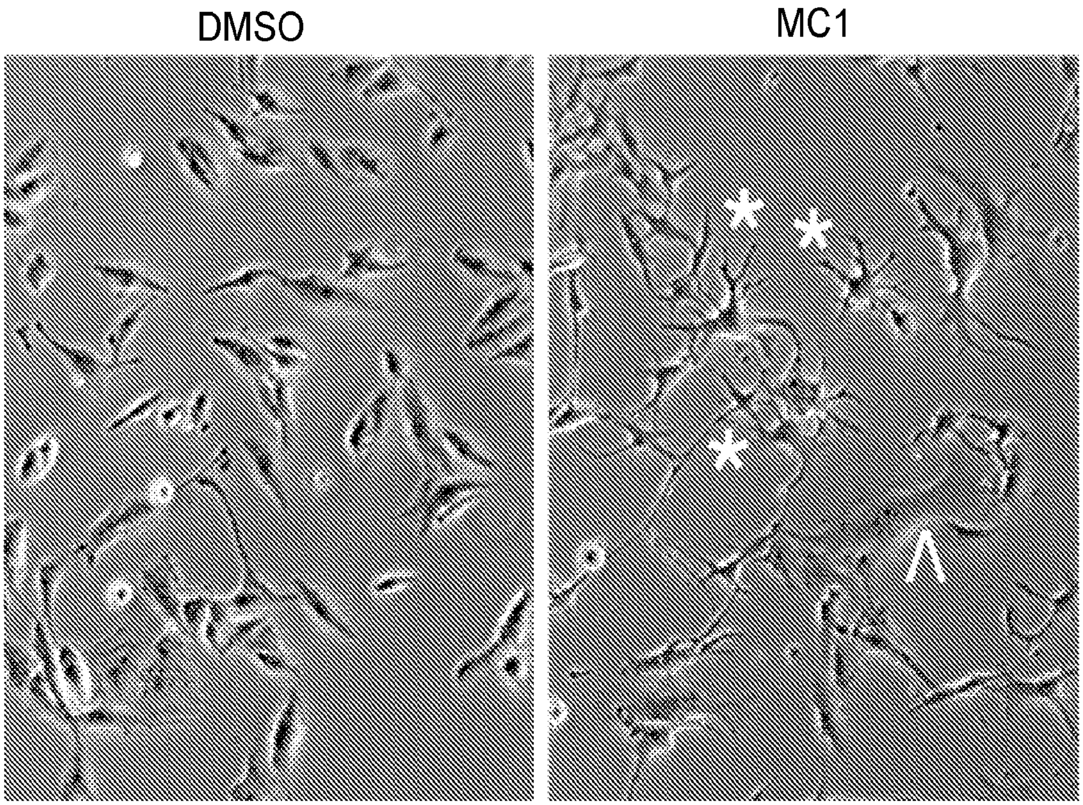
FIG. 3 depicts MC1 phenocopies TDG knockdown and has on-target activity, as demonstrated by elevation of 5fC and 5caC; Panel A: morphological changes induced by MC1, reminiscent of senescence (arrowhead), flat, multinucleated cells, and melanocyte differentiation (asterisks) cells with neuronal-like processes, phenocopy TDG knockdown. MC1 increases cellular level of 5fC (Panel B) and 5caC (Panel C) in genomic DNA, as assessed by immunofluorescence and immuno-dot blot, respectively; IF images were acquired with the same settings.
Figure 3:
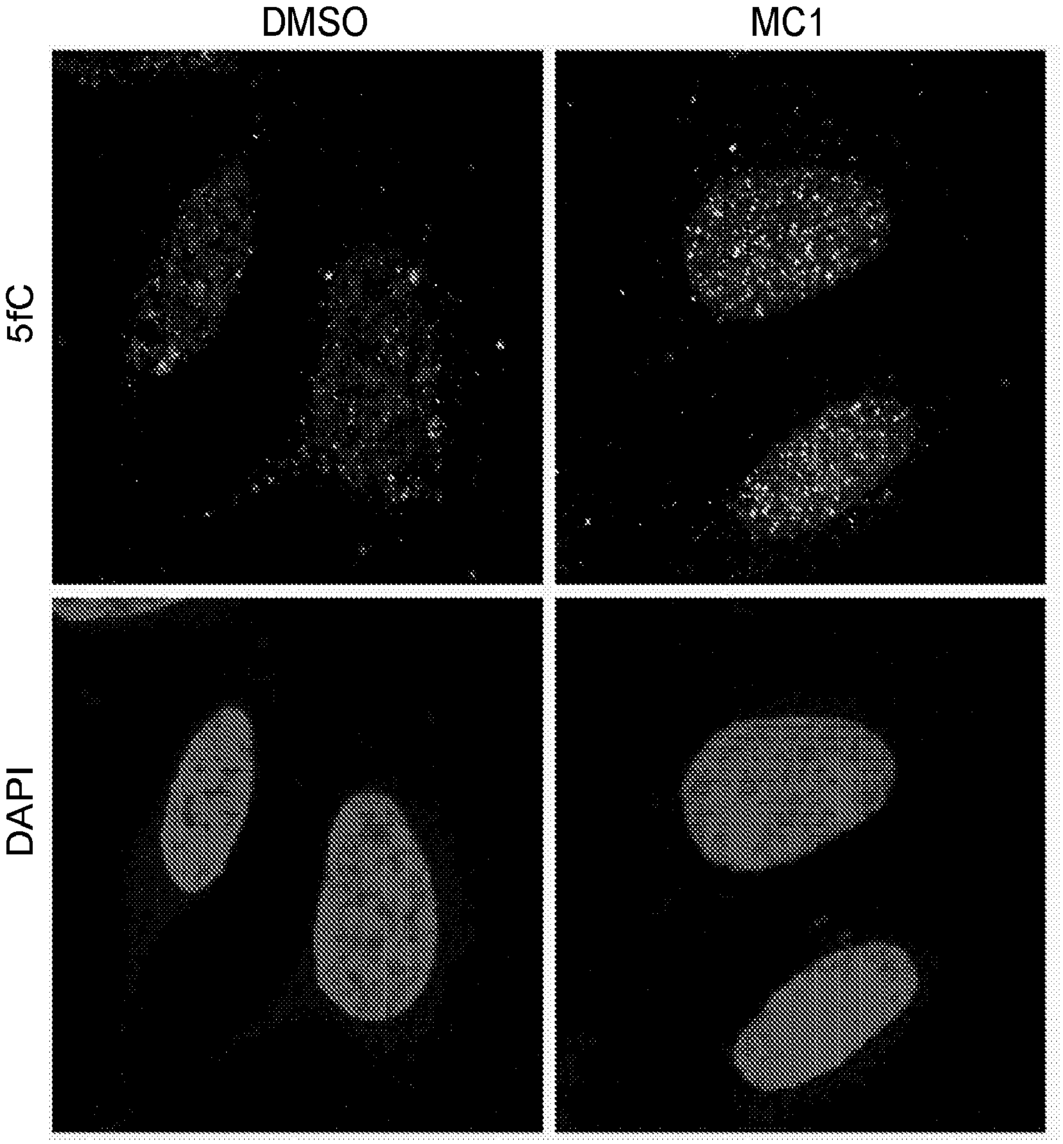
Figure 3:
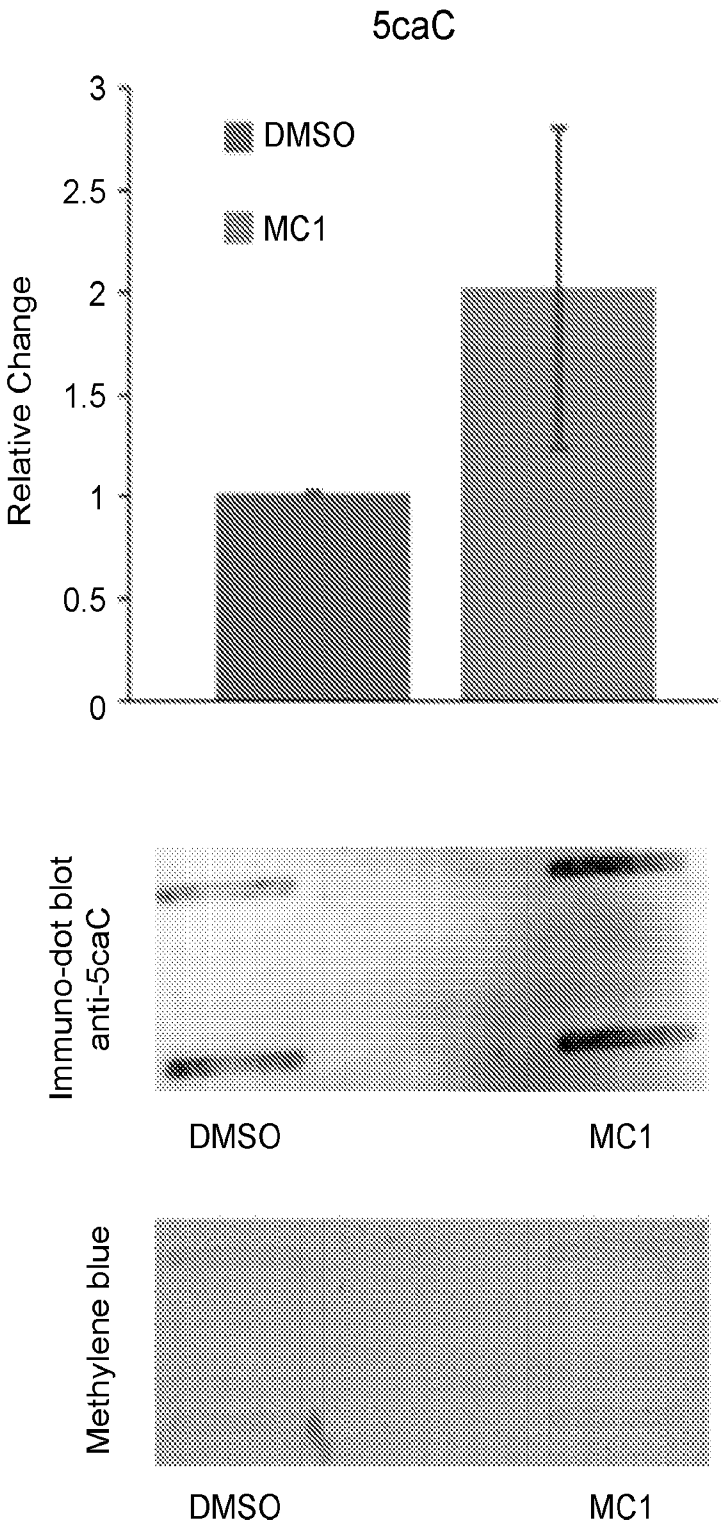

Example 5: MC1 Phenocopies TDG Knockdown and has On-Target Activity, as Demonstrated by Elevation of 5fC and 5caC MC1 recapitulated morphological changes previously described for TDG knockdown, and augmented cellular 5fC and 5caC levels (see, FIG. 3), a strong indication of on-target inhibition, as TDG is the main activity involved in 5caC removal (He et al., Science, 2011, 333, 1303-1307; and Maiti et al., J. Biol. Chem., 2011, 286, 35334-35338).

Figure 4:
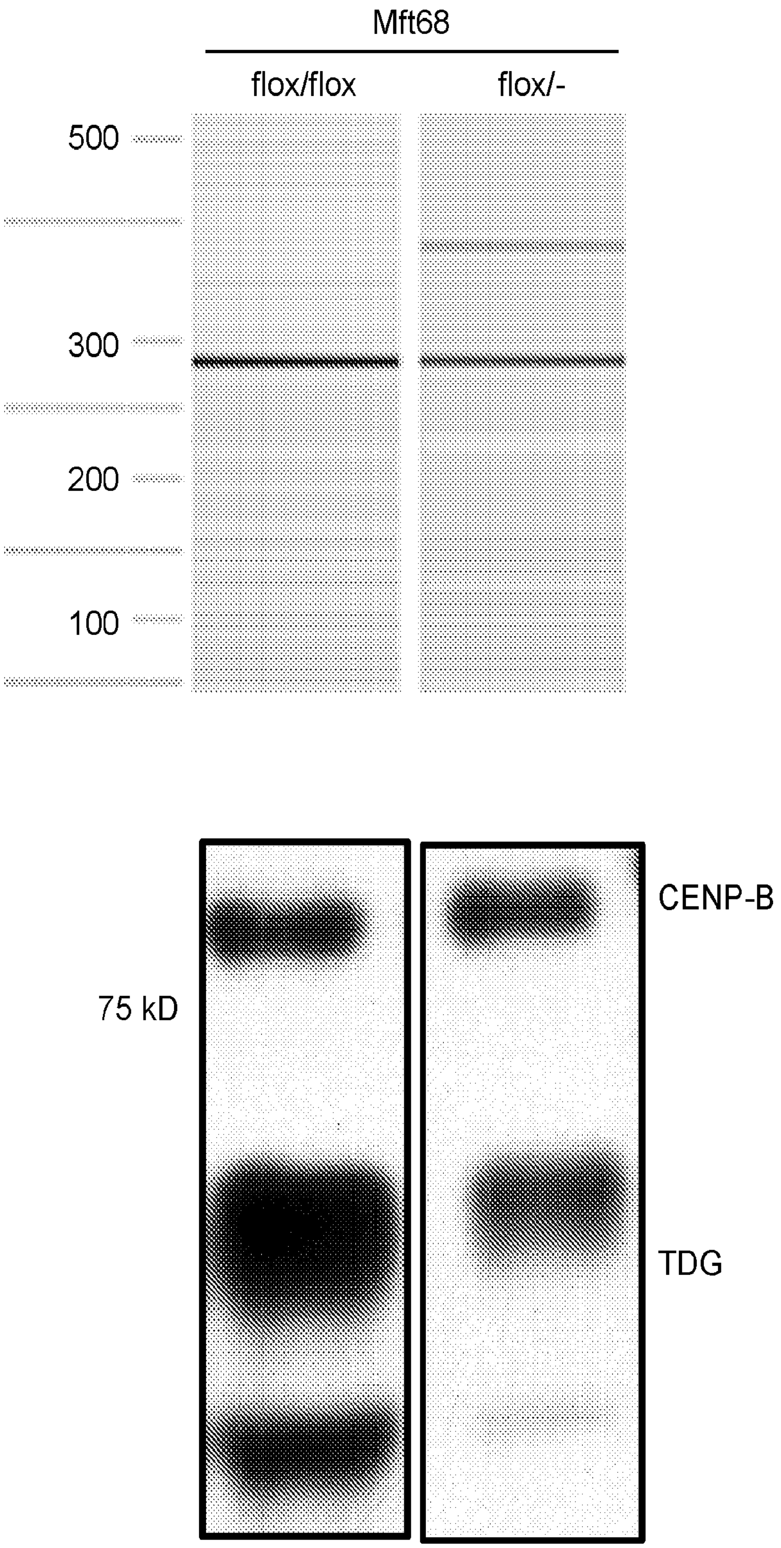
FIG. 4 depicts MC1 has on-target activity, as demonstrated by increased cytotoxicity on hemizygous vs. normal TDG content cells. Genotyping of Mft68 cells, showing the $TDG^{flox/flox}$ and $TDG^{flox/-}$ variants; by western blotting, $Mft68^{flox/-}$ cells express approximately half the amount of TDG protein compared to $Mft68^{flox/flox}$ cells; cell viability of $Mft68^{flox/flox}$ and $Mft68^{flox/-}$ cells in the presence of increasing concentrations of MC1; representative morphologic differences accompanying the reduction in cell viability in $Mft68^{flox/flox}$ and $Mft68^{flox/-}$ cells; estimated IC50 for cell killing is indicated.
Figure 4:
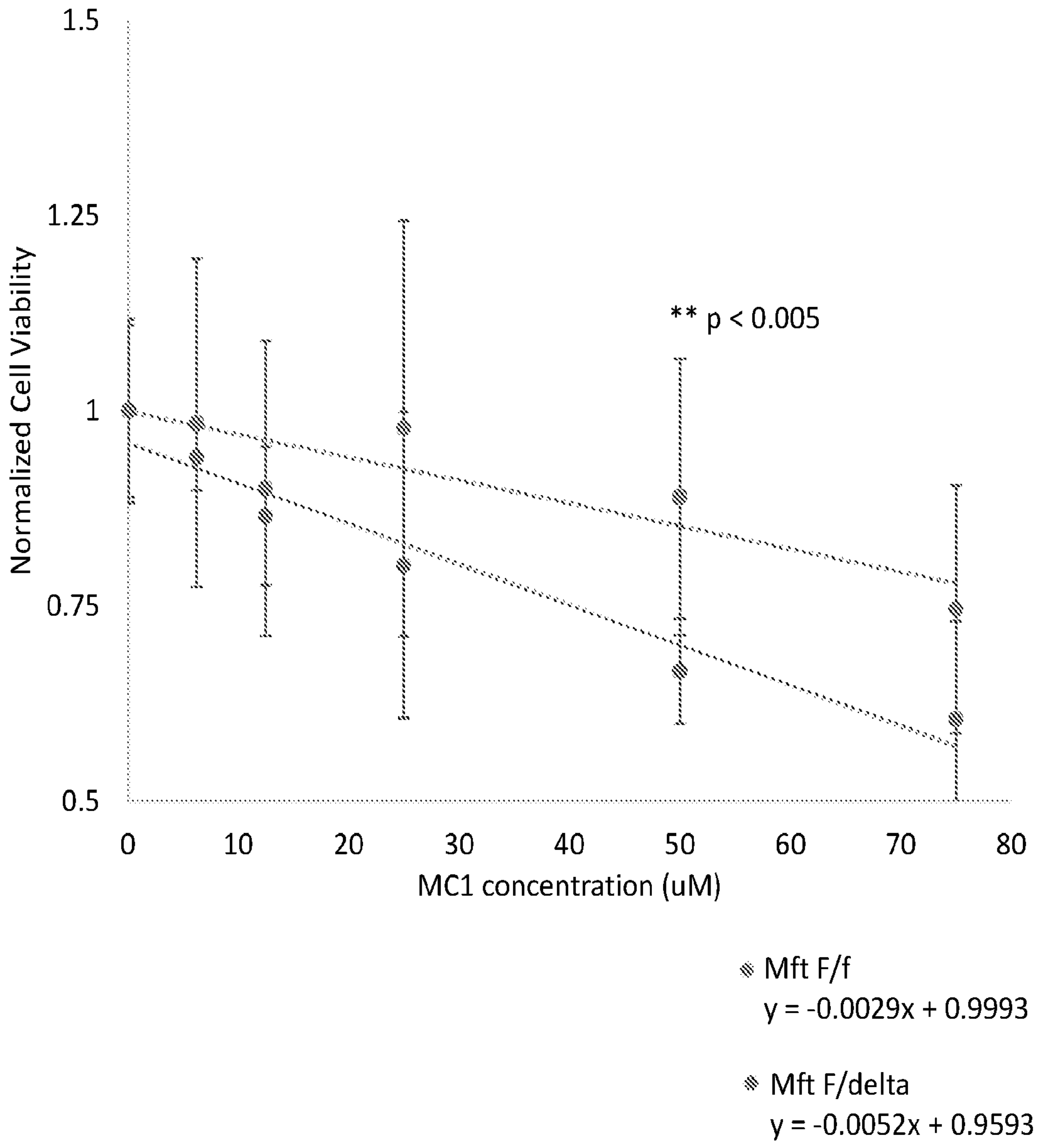
Figure 4:
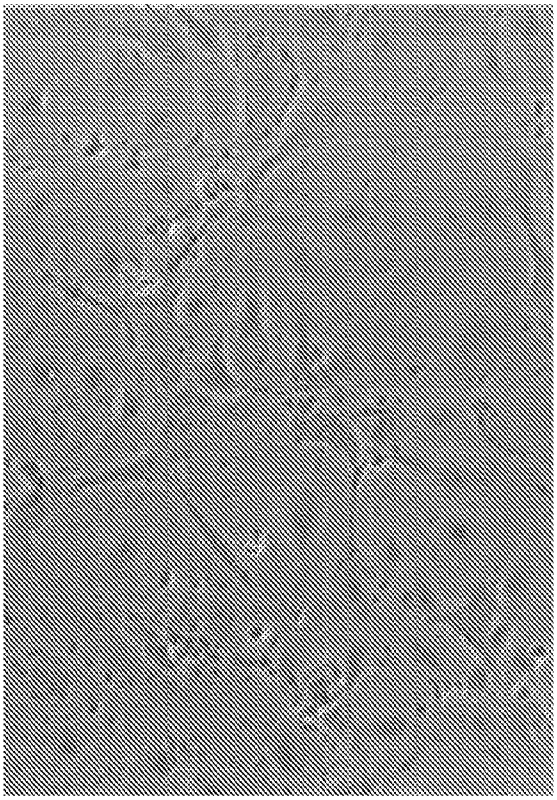
Figure 4:
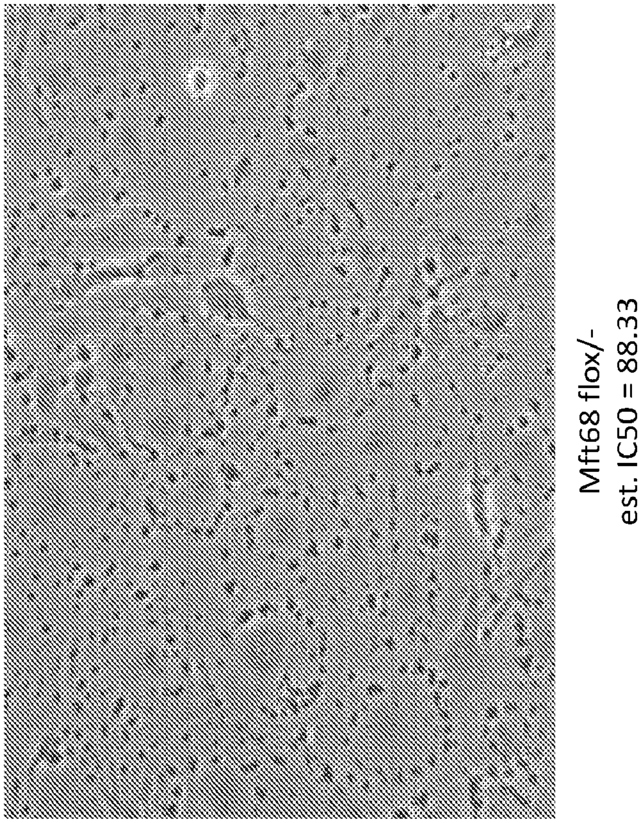

Example 6: MC1 has On-Target Activity, as Demonstrated by Increased Cytotoxicity on Hemizygous vs. Normal TDG Content Cells To further assess MC1 on-target activity in vivo, a pair of isogenic cell lines were generated from a tumor that originated spontaneously in a mouse containing an inducible Tdg deletion cassette. This allowed for direct comparison between normal TDG gene dosage ($Tdg^{flox/flox}$ genotype) and hemizygous TDG gene dosage ($Tdg^{flox/-}$ genotype). It was confirmed in the hemizygous cell line, $Mft68^{flox-}$, a 50% reduction in TDG protein level relative to the flox cell line, $Mft68^{flox/flox}$. The cell viability in the presence of increasing concentrations of MC1 was determined using a commercial assay. In keeping with on-target activity of MC1, the hemizygous Tdg cell line was more sensitive to MC1, with visible morphologic differences accompanying the reduction in cell viability (see, FIG. 4). These data are consistent with the fact that MC1 phenotypes are determined specifically by TDG protein inhibition.

Example 7: MC1 Induces Senescence of Cancer Cells

Figure 5:
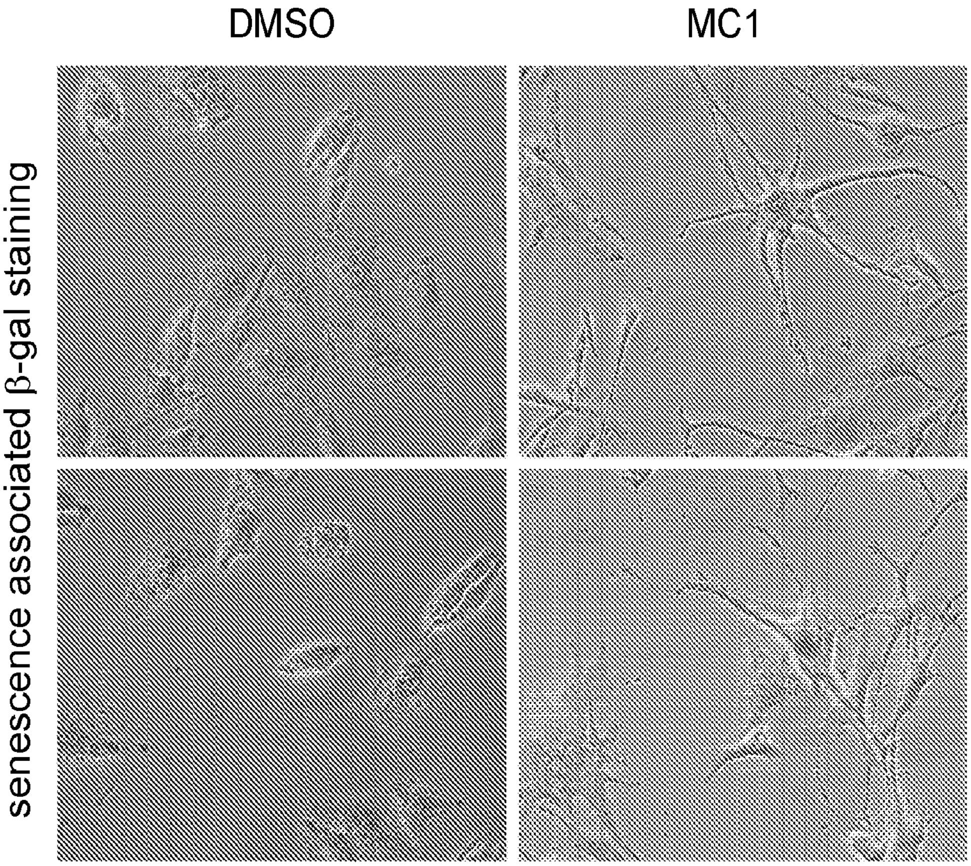
FIG. 5 depicts MC1 induces senescence of cancer cells; MC1 induces senescence of SK28 melanoma cells, as evidenced by (Panel A) senescence-associated beta-gal staining and (Panel B) detection of senescence-associated heterochromatin foci (SAHF, stained with H3K9me3); IF images were acquired with the same settings.
Figure 5:
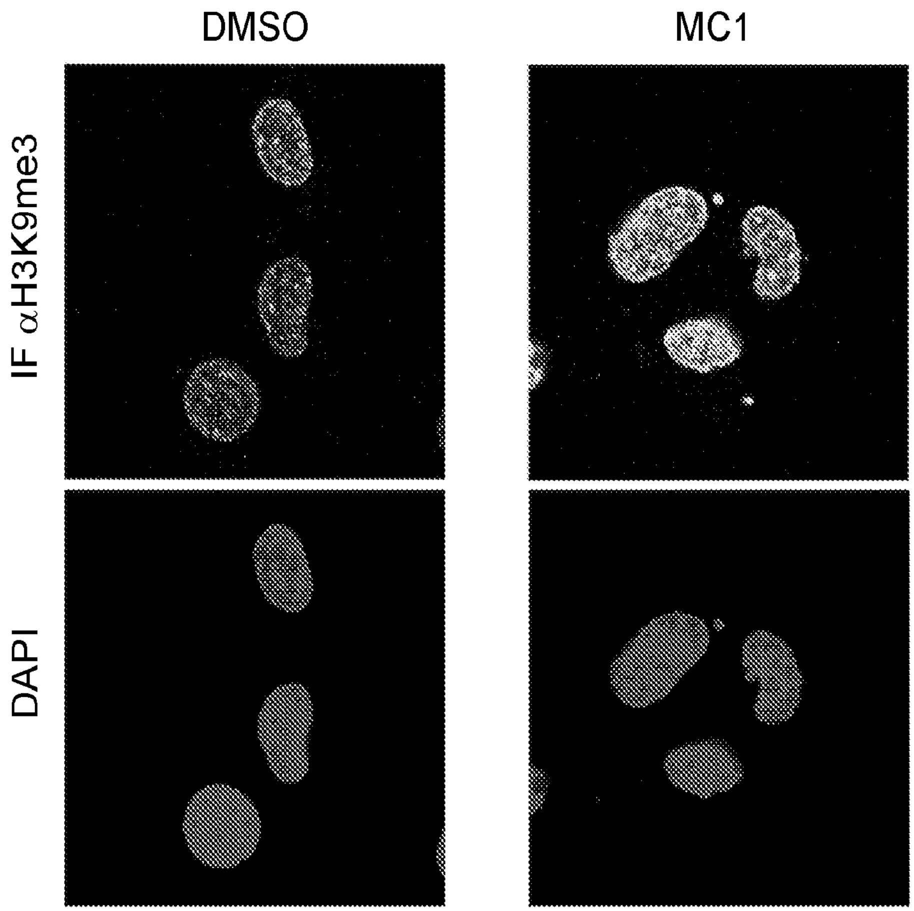

MC1 induced senescence, as detected by senescence-associated β-gal staining (see, FIG. 5, Panel A). Senescence is also linked to dramatic alterations of the chromatin landscape that is reorganized in facultative repressive structures known as senescence-associated heterochromatin foci (SAHF) (Narita et al., Cell, 2003, 113, 703-716; and Zhang et al., Mol. Cell. Biol., 2007, 27, 2343-2358). Senescent cells exhibited increased levels of repressive marks, such as H3K9me2/3 and H3K27me2/3 (Narita et al., Cell, 2003, 113, 703-716; and Ito et al., Cell Rep., 2018, 22, 3480-3492), which would predict decreased activating marks at these sites. Importantly, MC1 also induced SAHF, detected by immunofluorescence for H3K9me3 (see, FIG. 5, Panel B).

Example 8: MC1 Decreases Clonogenic Capacity of Cancer Cells

Figure 6:
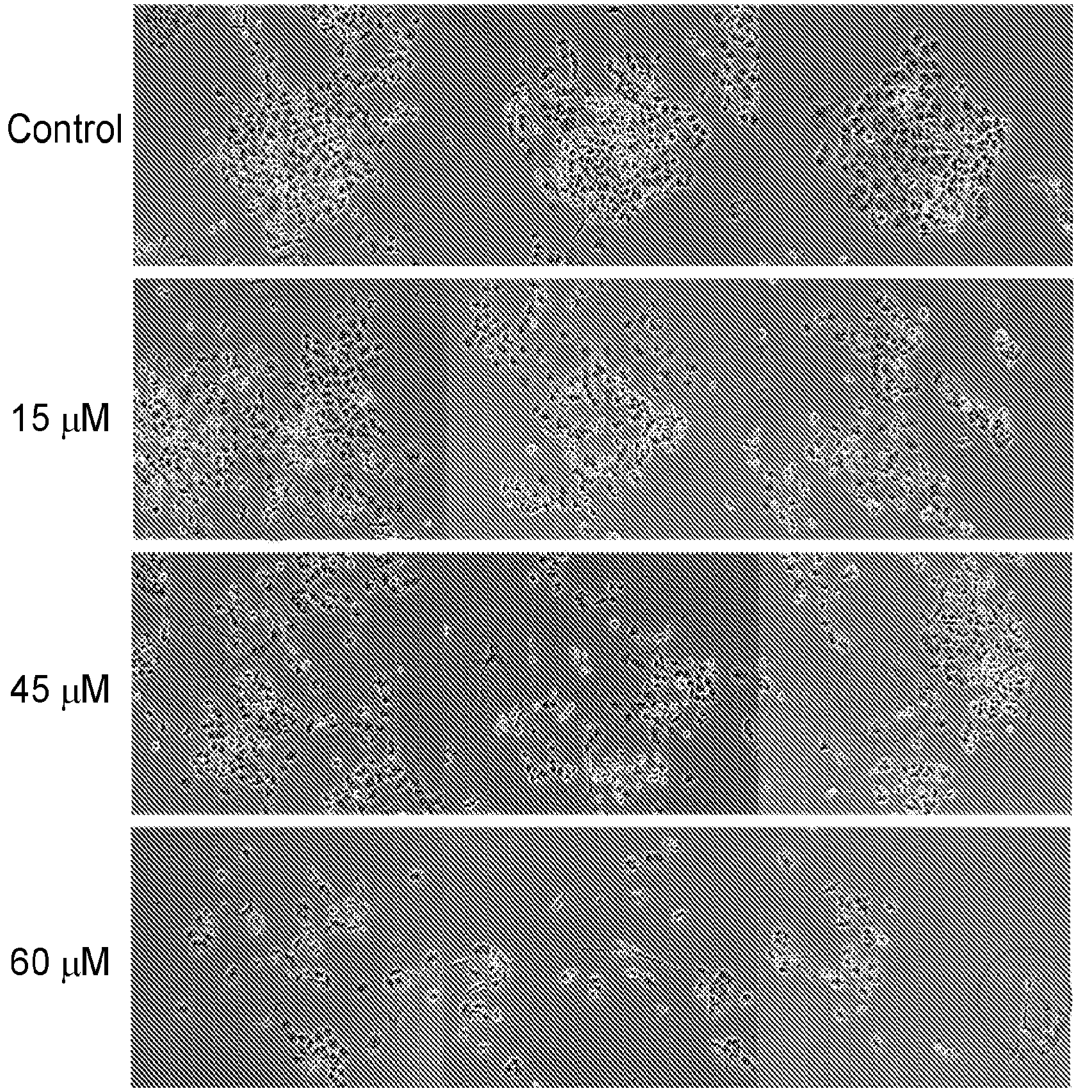
FIG. 6 depicts MC1 decreases clonogenic capacity of H23 lung cancer cells; Panel A: treatment of H23 lung cancer cells with the indicated concentrations of the TDG inhibitor MC1 decreases colony formation in a dose-dependent fashion; circles mark senescent cells that are flat or bearing long processes; Panel B: graph depicting colony formation by H23 cells, assessed at day 6 of treatment with the indicated concentrations of MC1.
Figure 6:
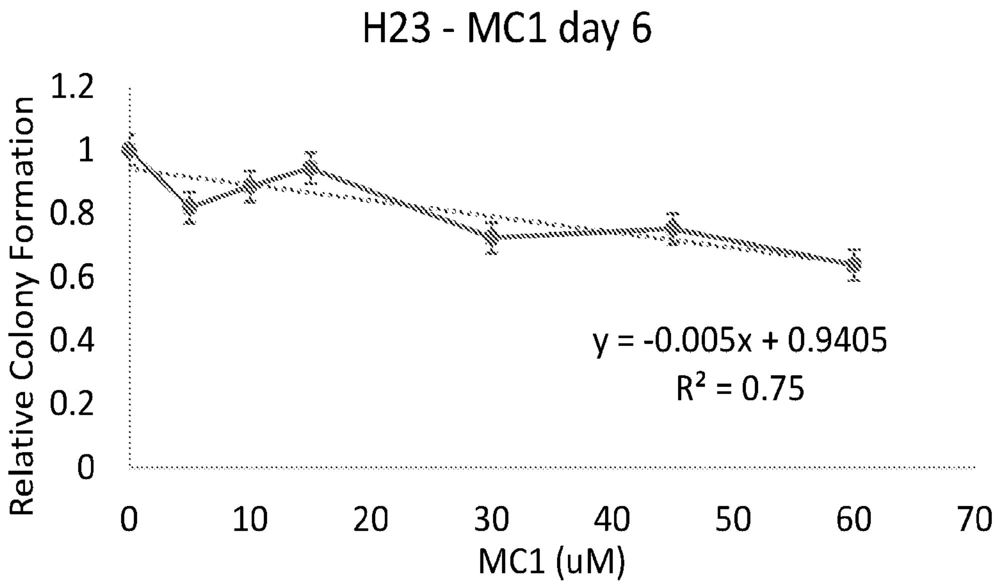
Figure 7:
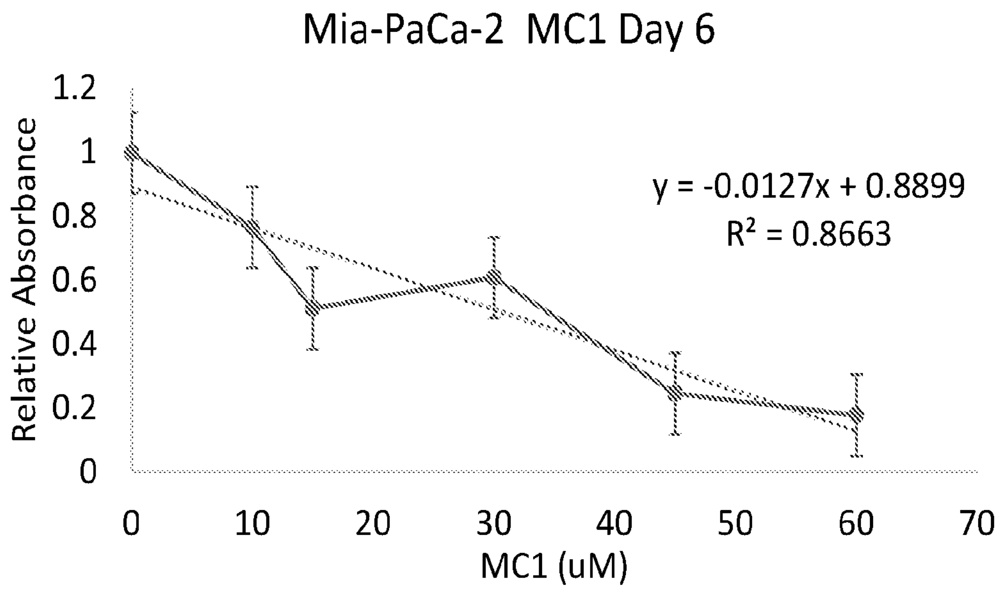
FIG. 7 depicts MC1 decreases clonogenic capacity of Mia-PaCa-2 pancreatic cancer cells; graph depicting colony formation by Mia-PaCa-2 cells, assessed at day 6 of treatment with the indicated concentrations of MC1.

MC1 treatment of the TDG-dependent H23 cell line, but not of the TDG-independent line A548, decreased clonogenic capacity, as colonies were reduced in number and size. Cells at the periphery of the colonies exhibited features of senescence (see, FIG. 6). MC1 treatment of MiaPaCa-2 pancreatic cancer cells also reduced clonogenic survival (see, FIG. 7).

Figure 8:
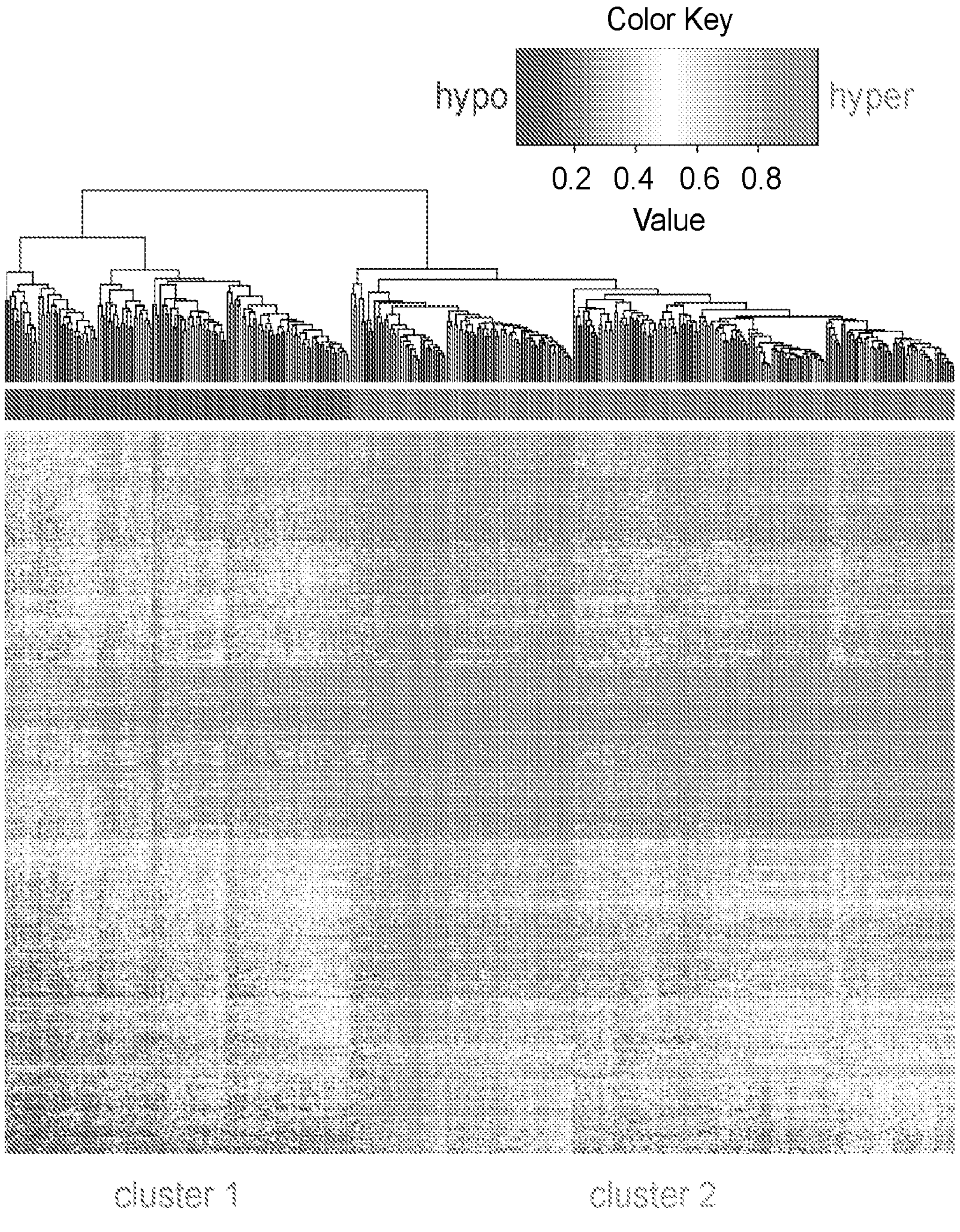
FIG. 8 depicts cluster analysis of metastatic SKCM methylation with 1,028 CpG sites demethylated in a TDG-dependent fashion (Panel A). Two dominant clusters are apparent which differ in the extent of TDG-mediated hypomethylation. By gene set variance analysis (GSVA), inflammatory genesets are under-represented (Panel B) and their score is lower (Panel C) in the prominently hypomethylated melanomas.
Figure 8:
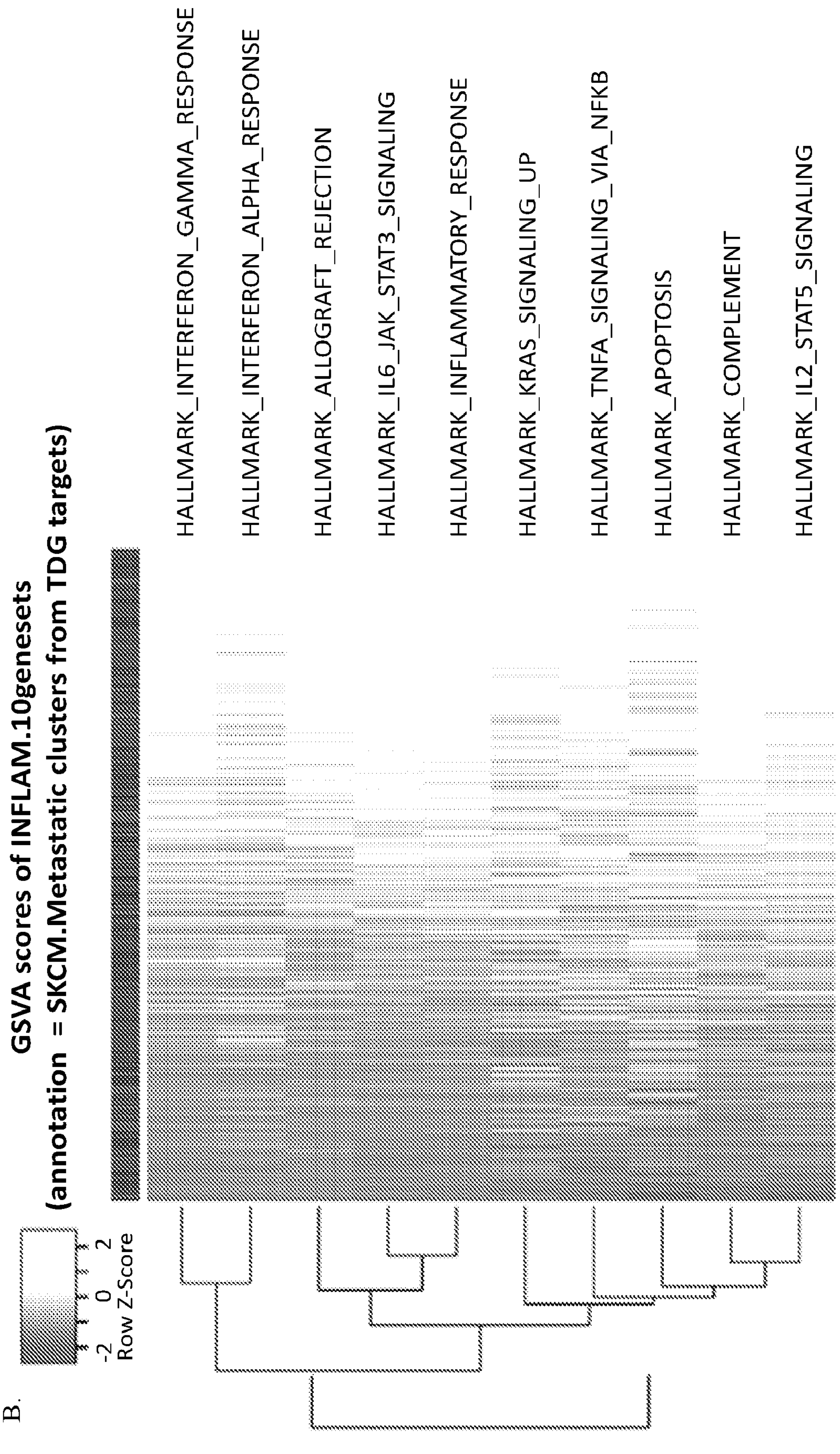
Figure 8:
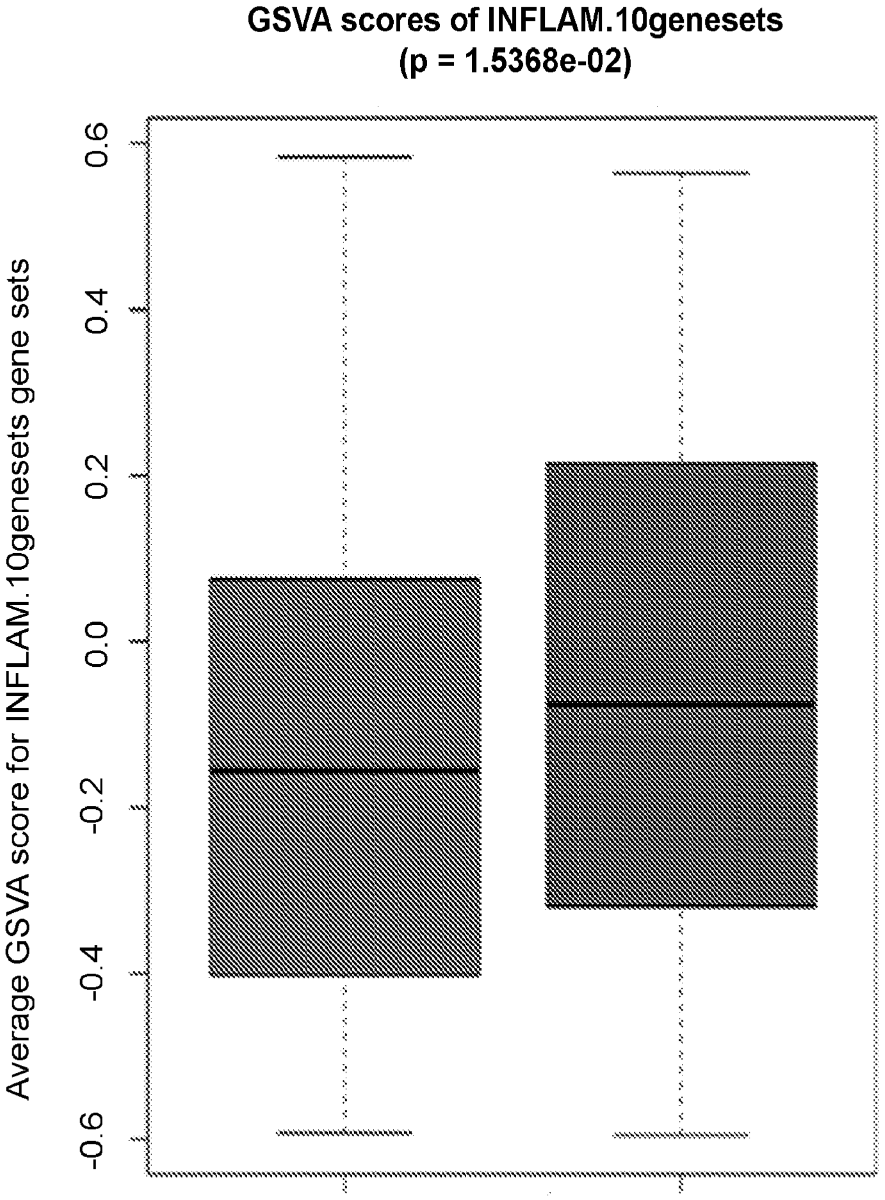

Example 9: TDG is an Immunomodulator that Suppresses Immune Response to Tumors Cluster analysis of metastatic SKCM methylation with 1.028 CpG sites demethylated in a TDG-dependent fashion was carried out. Two dominant clusters were apparent which differ in the extent of TDG-mediated hypomethylation (FIG. 8, Panel A). The gene set variance analysis (GSVA) demonstrated that inflammatory genesets are under-represented (FIG. 8, Panel B) and their score is lower (FIG. 8, Panel C) in the prominently hypomethylated melanomas. These data show that that melanomas with pervasive DNA hypomethylation are depleted of hallmarks of inflammatory signaling. JAK-STAT signaling and TNF signaling, thus confirming that prominent DNA hypomethylation driven by elevated TET-TDG activity correlates with immunoevasion. "cold" tumor status and resistance to immunotherapy. These data further support and strengthen TDG status as an immunomodulatory target.

Figure 9:
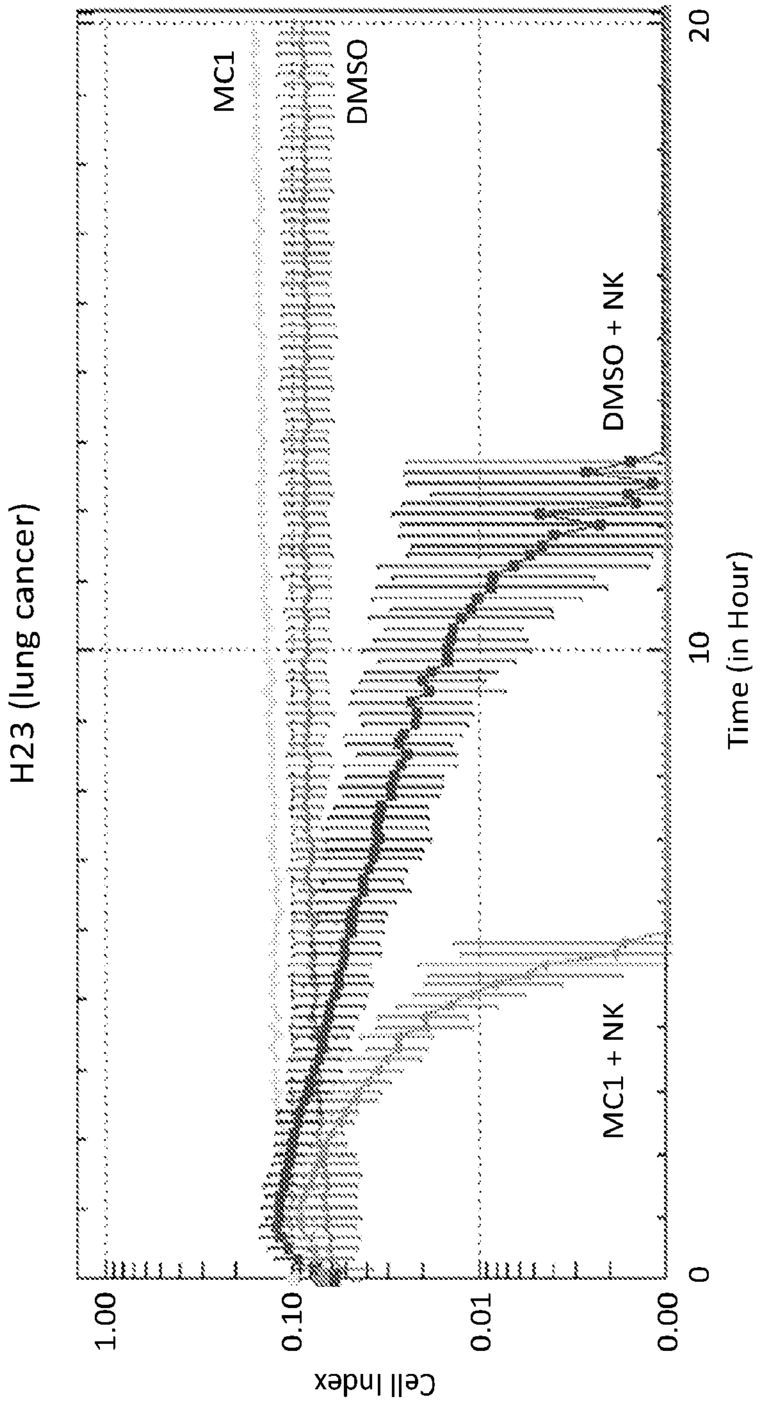
FIG. 9 depicts cell killing analysis over an incubation time of 20 hours by xCELLigence real-time cell analyzer: H23 lung cancer cells were treated with DMSO or MC1 for 3 days, and then incubated or not with NK92 natural killer cells, and monitored in real-time for loss (cytotoxicity) of the adherent H23 cells, as indicated. Experiments were performed in duplicate and are presented as average±standard deviation (Panel A). Cell killing analysis as assessed by contrast phase microscopy: SK28 melanoma cells were treated with DMSO or MC1 for 3 days, and then incubated or not with NK92 natural killer cells for 5 hours. Melanoma cells are spindle-shaped, NK cells are smaller and round (Panel B). Representative images are shown. Similar results were obtained with the lung cancer line H358.
Figure 9:
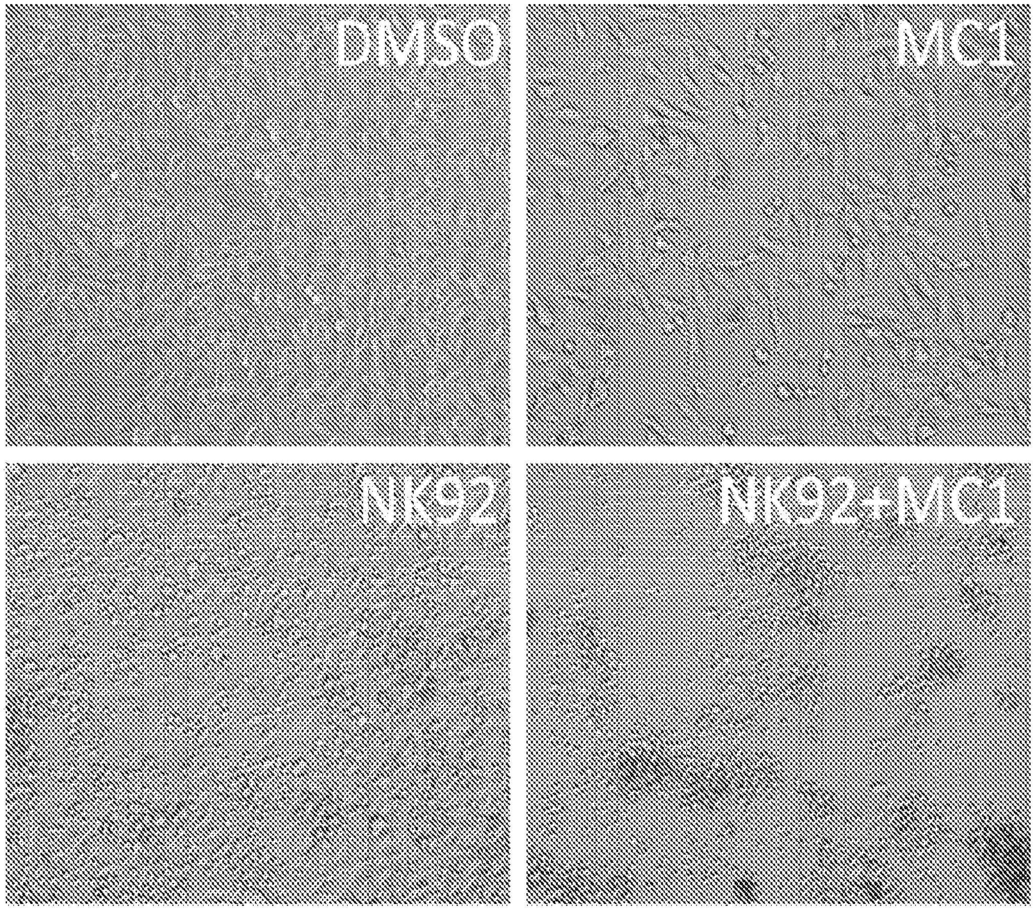

Example 10: TDG Inhibitor Renders Cancer Cells Susceptible to Innate Anti-Tumor Immune Response Melanoma SK28 cells and lung cancer H23 and H358 cells that are treated for 72 hours with the TDG inhibitor MC1 were killed more rapidly by the natural killer line NK92 than untreated samples. H23 lung cancer cells were treated with DMSO or MC1 for 3 days, and then incubated or not with NK92 natural killer cells, and monitored in real-time for loss (cytotoxicity) of the adherent H23 cells, as indicated. Experiments were performed in duplicate and are presented as average±standard deviation (FIG. 9, Panel A). The results were further confirmed in SK28 melanoma cells, which were treated with DMSO or MC1 for 3 days, and then incubated or not with NK92 natural killer cells for 5 hours. Melanoma cells were spindle-shaped, whereas NK cells were smaller and round (FIG. 9, Panel B). Similar results were obtained with the lung cancer line H358. These results suggest that inhibition of TDG can reprogram the hypomethylated epigenome of melanoma, induce senescence and proimmunogenic inflammation, thus sensitizing ICB-resistant cases to anti-PDI immunotherapy.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

What is claimed is:
1. A compound selected from the group consisting of:
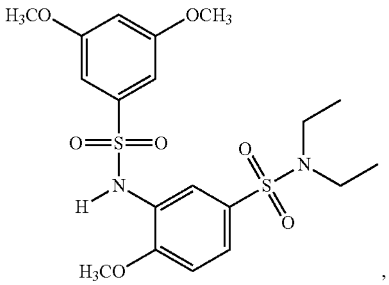
,
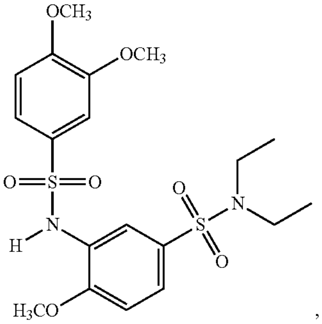
,
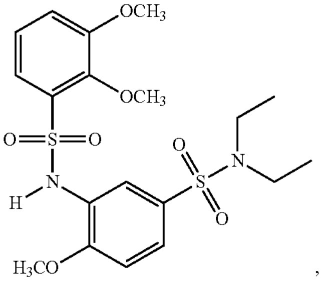
,
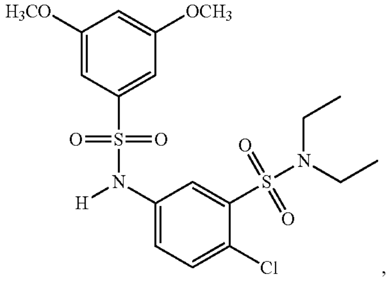
,
-continued
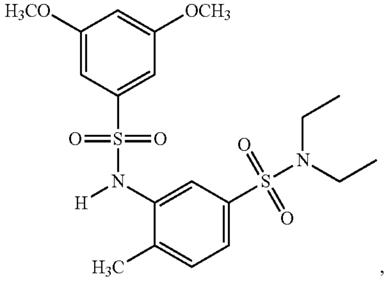
,
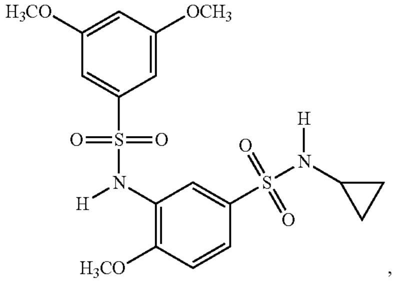
,
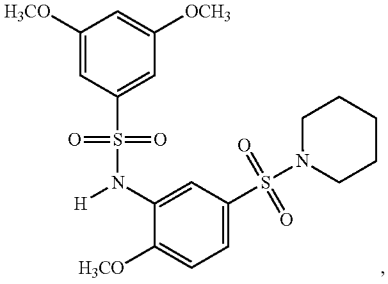
,
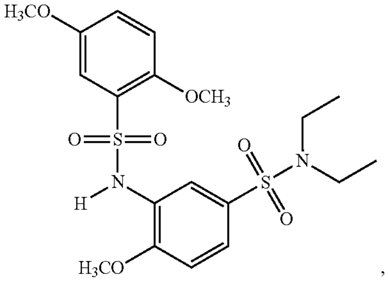
, -continued

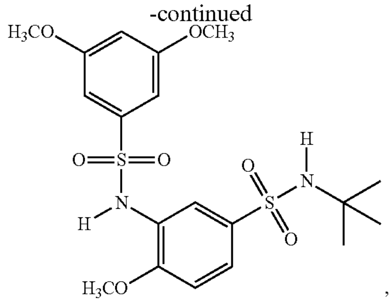

,

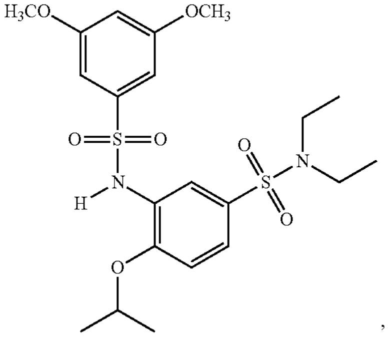

, and

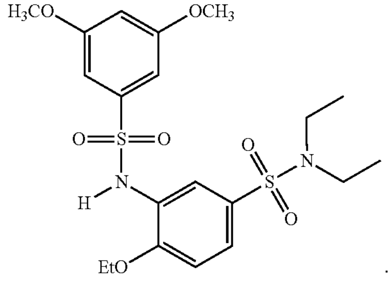

.

2. A compound having Formula I:

(I)

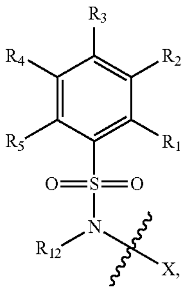

or a pharmaceutically acceptable salt thereof, wherein X is:

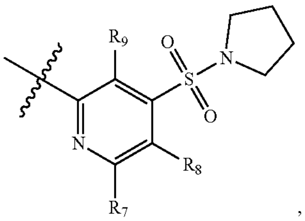

, each of $R_1$, $R_2$ $R_3$, $R_4$, and $R_5$ is, independently, selected from the group consisting of hydrogen, halogen, hydroxyl, cyano, nitro, substituted or unsubstituted alkyl, substituted or unsubstituted alkenyl, substituted or unsubstituted alkoxy, substituted or unsubstituted amine, substituted or unsubstituted alkylamino, substituted or unsubstituted aminoalkoxy, and substituted or unsubstituted alkylthiol, provided that at least one of $R_1$, $R_2$ $R_3$, $R_4$, and $R_5$ is unsubstituted $C_{1-3}$alkoxy; and each of $R_7$, $R_8$, $R_9$, and $R_{12}$ is, independently, selected from the group consisting of hydrogen, halogen, hydroxyl, cyano, nitro, substituted or unsubstituted alkyl, substituted or unsubstituted alkoxy, and substituted or unsubstituted amine.

3. The compound of claim 2, wherein each of $R_1$, $R_2$, $R_3$, $R_4$, and $R_5$ is, independently, hydrogen or unsubstituted $C_{1-3}$alkoxy.

4. The compound of claim 2, wherein each of $R_1$, $R_2$, $R_3$, $R_4$, and $R_5$ is, independently, hydrogen or $—OCH_3$.

5. The compound of claim 2, wherein the compound is:

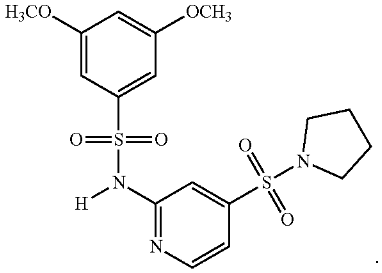 [SMILES: COc1cc(OC)cc(S(=O)(=O)Nc2cc(S(=O)(=O)N3CCCC3)ccn2)c1]

.

6. A pharmaceutical composition comprising the compound of claim 2, or a pharmaceutically acceptable salt thereof, and a pharmaceutically acceptable carrier.

7. A method of treating cancer in a mammal in need thereof, the method comprising administering to the mammal a compound having Formula I:

(I)

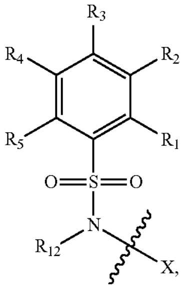

or a pharmaceutically acceptable salt thereof, wherein:

X is:

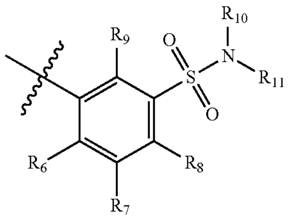

or

-continued

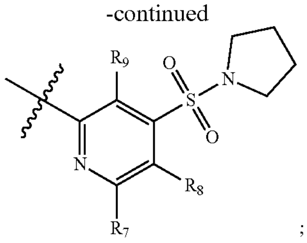

;

each of $R_1$, $R_2$ $R_3$, $R_4$, and $R_5$ is, independently, selected from the group consisting of hydrogen, halogen, hydroxyl, cyano, nitro, substituted or unsubstituted alkyl, substituted or unsubstituted alkenyl, substituted or unsubstituted alkoxy, substituted or unsubstituted amine, substituted or unsubstituted alkylamino, substituted or unsubstituted aminoalkoxy, and substituted or unsubstituted alkylthio, provided that at least one of $R_1$, $R_2$ $R_3$, $R_4$, and $R_5$ is unsubstituted $C_{1-3}$alkoxy;

$R_6$ is selected from the group consisting of hydrogen, halogen, hydroxyl, cyano, nitro, substituted or unsubstituted alkyl, substituted or unsubstituted alkoxy, substituted or unsubstituted amine, substituted or unsubstituted alkylamino, and substituted or unsubstituted aminoalkoxy;

each of $R_7$, $R_8$, $R_9$, and $R_{12}$ is, independently, selected from the group consisting of hydrogen, halogen, hydroxyl, cyano, nitro, substituted or unsubstituted alkyl, substituted or unsubstituted alkoxy, and substituted or unsubstituted amine; and $R_{10}$ and $R_{11}$ are, independently, selected from the group consisting of hydrogen, substituted or unsubstituted alkyl, and substituted or unsubstituted cycloalkyl, or together with the nitrogen to which they are bonded form a substituted or unsubstituted heteroaryl or a substituted or unsubstituted heterocycloalkyl;

wherein the cancer is selected from the group consisting of melanoma, prostate cancer, pancreatic cancer, breast cancer, colon cancer, lung cancer, ovarian cancer, and glioblastoma.

8. The method of claim 7, wherein X is:

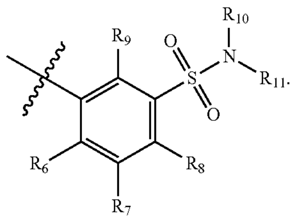

9. The method of claim 8, wherein each of $R_1$, $R_2$ $R_3$, $R_4$, and $R_5$ is, independently, hydrogen or —$OCH_3$.

10. A pharmaceutical composition comprising the compound of claim 1, or a pharmaceutically acceptable salt thereof, and a pharmaceutically acceptable carrier.

* * * * *

SEQUENCE LISTING

<160> NUMBER OF SEQ ID NOS: 2

<210> SEQ ID NO 1
<211> LENGTH: 43
<212> TYPE: DNA
<213> ORGANISM: Artificial Sequence -continued
<220> FEATURE:
<223> OTHER INFORMATION: Synthetic Construct
<220> FEATURE:
<221> NAME/KEY: modified_base
<222> LOCATION: (6)..(6)
<223> OTHER INFORMATION: residue 6 is uracil
<400> SEQUENCE: 1
ccacttgtga attgacagcc catgtgcatc aattcacgag tgg 43
<210> SEQ ID NO 2
<400> SEQUENCE: 2
000